(12) United States Patent
Viens et al.

(10) Patent No.: US 9,808,143 B2
(45) Date of Patent: Nov. 7, 2017

(54) OPTOGENETIC PROBE

(71) Applicant: UNIVERSITE LAVAL, Québec (CA)

(72) Inventors: Jean-François Viens, Québec (CA);
Jean-François Gravel,
Stoneham-et-Tewkesbury (CA); Younès Messaddeq, Québec (CA); Yannick Ledemi, Québec (CA); Maxime Rioux, Sainte-Foy (CA)

(73) Assignee: UNIVERSITE LAVAL, Quebec (CA)

( * ) Notice: Subject to any disclaimer, the term of this patent is extended or adjusted under 35 U.S.C. 154(b) by 581 days.

(21) Appl. No.: 14/409,390

(22) PCT Filed: Jun. 18, 2013

(86) PCT No.: PCT/CA2013/050467
§ 371 (c)(1),
(2) Date: Dec. 18, 2014

(87) PCT Pub. No.: WO2013/188973
PCT Pub. Date: Dec. 27, 2013

(65) Prior Publication Data
US 2015/0141844 A1    May 21, 2015

Related U.S. Application Data

(60) Provisional application No. 61/661,028, filed on Jun. 18, 2012.

(51) Int. Cl.
*G02B 6/44* (2006.01)
*A61B 1/00* (2006.01)
(Continued)

(52) U.S. Cl.
CPC ........ *A61B 1/0017* (2013.01); *A61B 1/00114* (2013.01); *A61B 1/015* (2013.01);
(Continued)

(58) Field of Classification Search
None
See application file for complete search history.

(56) References Cited

U.S. PATENT DOCUMENTS 5,419,312 A    5/1995 Arenberg et al.
5,643,250 A    7/1997 O'Donnell, Jr.
(Continued)

OTHER PUBLICATIONS

Lechasseur et al., "A microprobe for parallel optical and electrical recordings from single neurons in vivo". Nature Methods, vol. 8, No. 4, pp. 319-325 (2011).
(Continued)

*Primary Examiner* — Tina Wong
(74) *Attorney, Agent, or Firm* — Hovey Williams LLP

(57) ABSTRACT

An optogenetic probe, an optogenetic system, and a method for fabricating an optogenetic probe are provided. The optogenetic probe has a proximal and a distal end, and includes an elongated body made of a body glass material and extending longitudinally between the proximal and distal ends. The optogenetic probe also includes at least one optical channel, each including an optical channel glass material having a refractive index larger than a refractive index of the body glass material, so as to guide light therealong. The optogenetic probes also includes at least one electrical channel, each including an electrical channel structure having an electrical conductivity larger than the electrical conductivity of the body glass material, so as to conduct electricity therealong. The optogenetic probe further includes at least one fluidic channel, each adapted for transporting fluid therealong. Each optical, electrical and fluidic channel extends longitudinally within the elongated body.

24 Claims, 7 Drawing Sheets

(51) Int. Cl.
*A61B 5/0476* (2006.01)
*A61B 1/015* (2006.01)
*C03B 37/012* (2006.01)
*C03B 37/026* (2006.01)
*C03B 37/027* (2006.01)
*G02B 6/42* (2006.01)
*G02B 6/43* (2006.01)
*B82Y 30/00* (2011.01)
*A61B 5/00* (2006.01)

(52) U.S. Cl.
CPC .......... *A61B 5/0071* (2013.01); *A61B 5/0084* (2013.01); *A61B 5/0476* (2013.01); *C03B 37/01211* (2013.01); *C03B 37/026* (2013.01); *C03B 37/02763* (2013.01); *C03B 37/02781* (2013.01); *G02B 6/4274* (2013.01); *G02B 6/43* (2013.01); *A61B 5/6847* (2013.01); *B82Y 30/00* (2013.01); *C03B 2203/16* (2013.01); *C03B 2203/34* (2013.01)

(56) References Cited

U.S. PATENT DOCUMENTS

| | | | |
|---|---|---|---|
| 5,723,819 A | 3/1998 | Kirma et al. | |
| 6,347,172 B1* | 2/2002 | Keller | G02B 6/0006 385/102 |
| 6,432,851 B1 | 8/2002 | Aitken | |
| 6,520,955 B2 | 2/2003 | Reynard | |
| 6,568,219 B1 | 5/2003 | Glass et al. | |
| 6,995,101 B2 | 2/2006 | Zou et al. | |
| 7,158,703 B2* | 1/2007 | Mjelstad | G02B 6/4427 385/101 |
| 7,292,758 B2 | 11/2007 | Bayindir et al. | |
| 7,773,647 B2 | 8/2010 | Messaddeq et al. | |
| 7,837,654 B2 | 11/2010 | Shumate et al. | |
| 7,846,391 B2 | 12/2010 | Jaffe et al. | |
| 7,883,536 B1 | 2/2011 | Bendett et al. | |
| 9,010,439 B2* | 4/2015 | Fogg | H01B 7/045 166/344 |
| 9,190,184 B2* | 11/2015 | Nelson | B29C 70/523 |
| 9,330,816 B2* | 5/2016 | Deighton | H01B 7/045 |
| 9,472,314 B2* | 10/2016 | Kachmar | H01B 1/026 |
| 2011/0094584 A1 | 4/2011 | Sawada et al. | |
| 2012/0281953 A1* | 11/2012 | Choi | G02B 6/441 385/101 |
| 2013/0011106 A1* | 1/2013 | Congdon, II | G02B 6/44 385/101 |
| 2015/0041171 A1* | 2/2015 | Heggdal | H01B 7/045 174/15.6 |
| 2015/0234143 A1* | 8/2015 | Smith | G02B 6/4494 702/2 |
| 2015/0342690 A1* | 12/2015 | Zubiate | A61B 18/22 606/130 |

OTHER PUBLICATIONS

The Written Opinion of the International Searching Authiority in the corresponding PCT/CA2013/050467 application, filed Jun. 18, 2013.

* cited by examiner

OPTOGENETIC PROBE

RELATED APPLICATIONS

This is a national stage application under 35 U.S.C. §371 of International Application No. PCT/CA2013/050467, filed Jun. 18, 2013, which claims priority from U.S. Provisional Patent Application No. 61/661,028 filed Jun. 18, 2012. The disclosures of the above-referenced applications are hereby incorporated into the present application by reference in their entirety.

FIELD OF THE INVENTION

The present invention relates to the field of optogenetics, and more particularly concerns an optogenetic probe and system, and a method for fabricating the optogenetic probe.

BACKGROUND OF THE INVENTION

Optogenetics, as known in the art of neuroscience and electro-physiology, is the combination of genetic and optical methods to control specific events in targeted cells of living tissue, particularly within living organisms such as mammals and other animals, with the temporal and spatial precision needed to keep pace with functioning intact biological systems. Millisecond-scale temporal precision and micrometer-scale spatial resolution are central to optogenetics. This allows experimenters to keep pace with fast biological information processing, for example, by probing the causal role of specific action potential patterns in defined neurons.

In electro-physiology, an action potential is a short-lasting event in which the electrical membrane potential of a cell or neuron rapidly rises and falls within a voltage range of about 100 micro-volts. Action potentials occur in several types of animal cells, called excitable cells, which include neurons, muscle cells, and endocrine cells, as well as some plant cells. Action potentials may be recorded with small metal electrodes placed next to a cell or neuron, but a main problem of this approach is that of obtaining electrodes small enough to record voltages within a single axon without perturbing it, and that of overcoming the electrical capacitance effects of the cell or neuron.

Optical imaging technologies have been developed in recent years to measure action potentials using voltage-sensitive dyes. Such optogenetic technologies involve the combination of optical, electrical and fluidic functionalities all at once for the study and control of action potentials in living organisms. The hallmark of optogenetics is the introduction of fast light-activated channels that allow for the temporally precise manipulation of electrical and biochemical events while maintaining cell-type spatial resolution.

Optogenetics typically operates at the millisecond timescale to allow for the monitoring, the addition or the deletion of precise activity patterns within specific cells in the brains of intact animals, including mammals. By comparison, the temporal precision of traditional genetic manipulations conventionally employed to probe the causal role of specific genes within cells, via "loss-of-function" or "gain of function" changes in these genes is rather slow, from hours to days.

Optogenetics typically also operates at the micrometer scale to allow for spatial resolution of precise activity patterns, for example within specific cells in the brains of intact animals, including mammals. By comparison, the spatial resolution of bundles traditionally used in optogenetics, including electrodes, tubules and fiber-optic bundles, is of the order of 1 millimeter at best, which is inappropriate to resolve features as small as a cell or a neuron.

Today's optogenetics technology generally borrows the technology used in endoscopy which employs large, millimeter-scale assemblies of fiber-optic bundles, metallic wires and fluidic tubules, or a partial combination thereof, that do not meet the spatial resolution nor the minimalist invasion required for probing living tissues.

U.S. Pat. No. 5,419,312 issued to I. K. Arenberg provides a multi-functional endoscope apparatus which includes a specialized system for illuminating the interior of a body cavity and directing the resulting images outwardly from the cavity for observation. It also includes a sub-system for delivering laser light to the body cavity for treatment purposes in a safe and effective manner for both the patient and treating physician, and it incorporates a sub-system for sensing temperature and fluid pressure levels within a body cavity, and a sub-system for sensing electrical potentials generated within tissues. This document addresses the need for an endoscope system suitable for use in narrow body cavities, such as the inner ear, but does not meet the requirement of micrometer-scale resolution for sensing individual cells or neurons as required in optogenetics.

Medical procedures employing probes inserted into a patient's organs borrow the technology of laser probes for eye surgery as illustrated in U.S. Pat. No. 5,643,250 (the '250 patent), issued to F. E. O'Donnell, Jr., and in U.S. Pat. No. 6,520,955 (the '955 patent), issued to M. Reynard.

The '250 patent discloses a laser probe which includes a fiber-optic channel and an infusion port for irrigating solutions to be infused into an eye during laser surgery on cornea tissue. However, the laser probe diameter may not allow insertion through numerous layers and densities of tissues disposed between a dermal surface and internal organs disposed medially within a patient.

The '955 patent discloses a process and apparatus for removing cataract tissue in an eye and for injecting a lens replacement material into the eye lens to fill the intralenticular space. The apparatus disclosed in the '955 patent includes a needle having dual cannula oriented as coaxial annular conduits through which chemicals and enzymes are delivered into cataract tissue. A separate focused laser is used to destroy the cataract tissue, followed by decomposed cataract tissue being removed by aspiration through an aspiration instrument or through a coaxial annular conduit of the needle.

However, the '250 and the '955 patents do not provide means for impressing electrical voltage or electrical current to the tissue which is a desirable feature in optogenetics.

U.S. Pat. No. 7,292,758 issued to M. Bayindir provides a fiber photodetector comprising: a semiconducting element having a fiber length and being characterized as a non-composite semiconducting chalcogenide glass material selected from the group consisting of $(As_{40}Se_{60})_{1-x}Sn_x$, $As_{40}Se_{50}Te_{10}Sn_5$, and $As_2Se_3$, in at least one fiber direction; at least one pair of conducting electrodes in contact with the semiconducting element along the fiber length; and an insulator along the fiber length. Although this fiber can be scaled down to address some optogenetics applications, fluidic functionalities are not provided. In addition, the fiber photodetector disclosed in this patent raises serious concerns regarding the toxicity of the arsenic-based glass compositions therein.

A recent publication by Y. LeChasseur et al. in *Nature Methods*, vol. 8 no. 4, p. 319 (2011) describes the development of an optogenetic unit for electro-physiology comprising a dual optical core and an electrolyte-filled electrical core. This design enables the fabrication of optogenetic probes as small as 10 µm, combining electrical and optical detection with single-cell optical resolution at a depth of >6,000 µm in the intact central nervous system. However, the probes exhibit very high electrical resistance (6-26 MOhm), which may limit certain types of recordings due to insufficient signal-to-noise ratio. Moreover, there are no provisions for fluidic delivery functionalities.

Also known in the art are the following patents and patent applications:

| | |
|---|---|
| U.S. Pat. No. 7,773,647 | U.S. Pat. No. 7,846,391 |
| U.S. Pat. No. 7,837,654 | U.S. Pat. No. 6,568,219 |
| U.S. Pat. No. 6,432,851 | U.S. Pat. No. 6,995,101 |
| U.S. Pat. Pub. No. 2011/0094584A1 | |

In light of the above, it can be seen that existing optogenetic devices and methods lack the full set of attributes desired for providing a functional and minimally-invasive optogenetic probe. There is therefore a need in the fields of neuroscience and electro-physiology for an optogenetic probe that overcome or at least alleviates at least some of these drawbacks.

SUMMARY OF THE INVENTION

According to an aspect of the invention, there is provided an optogenetic probe having a proximal and a distal end. The optogenetic probe includes:
  an elongated body made of a body glass material having a refractive index and an electrical conductivity, the elongated body extending longitudinally between the proximal and distal ends of the optogenetic probe;
  at least one optical channel extending longitudinally within the elongated body and including an optical channel glass material having a refractive index larger than the refractive index of the body glass material, so as to guide light therealong;
  at least one electrical channel extending longitudinally within the elongated body and including an electrical channel structure having an electrical conductivity larger than the electrical conductivity of the body glass material, so as to conduct electricity therealong; and
  at least one fluidic channel extending longitudinally within the elongated body and adapted for transporting fluid therealong.

Advantageously, the optogenetic probe according to this aspect of the invention combines optical, electrical and fluidic functionalities all at once, which allows studying and controlling action potentials in living organisms and control of cellular function within intact animals. In some embodiments, the optical transparency and electrical conductivity of the optogenetic probe provides means of collecting optical and electrical information with millisecond timescale resolution, while fluidic channels within the body of the optogenetic probe provide means for the delivery of fluids within living tissues. Furthermore, in some embodiments, the distal end of the optogenetic probe may be tapered, or scaled down in size, in order to provide micrometer-scale spatial resolution with minimal disruption to surrounding living tissues.

Preferably, the optogenetic probe according to embodiments of the present invention is composed of a glass material that can be drawn into an elongated glass fiber; and that integrates optical, electrical and fluidic functionalities into a small cross-section for non-invasive insertion into a living organism.

According to another aspect of the invention, there is provided an optogenetic system including:
  an optogenetic probe having a proximal and a distal end, the optogenetic probe including:
    an elongated body made of a body glass material having a refractive index and an electrical conductivity, the elongated body extending longitudinally between the proximal and distal ends of the optogenetic probe;
    at least one optical channel extending longitudinally within the elongated body and including an optical channel glass material having a refractive index larger than the refractive index of the body glass material, so as to guide light therealong;
    at least one electrical channel extending longitudinally within the elongated body and including an electrical channel structure having an electrical conductivity larger than the electrical conductivity of the body glass material, so as to conduct electricity therealong; and
    at least one fluidic channel extending longitudinally within the elongated body and adapted for transporting fluid therealong;
  an optical module optically coupled to each optical channel;
  an electrical module electrically coupled to each electrical channel; and
  a fluidic module coupled to each fluidic channel.

According to a further aspect of the invention, there is provided a method of fabricating an optogenetic probe. The method includes the steps of:
  a) fabricating a fiber preform including:
    an elongated body made of a body glass material having a refractive index, an electrical conductivity, a softening temperature and a coefficient of thermal expansion;
    at least one optical channel including an optical channel glass material having a refractive index larger than the refractive index of the glass body material, so as to transmit light therealong, and a glass softening temperature and a coefficient of thermal expansion respectively similar to the glass softening temperature and coefficient of thermal expansion of the body glass material;
    at least one electrical channel including an electrical channel structure having an electrical conductivity larger than the electrical conductivity of the body glass material, so as to conduct electricity therealong; and
    at least one fluidic channel adapted for transporting fluid therealong; and
  b) drawing the fiber preform into the optogenetic probe.

Advantageously, the method according to this aspect of the invention uses cost-effective glass melt techniques and industrial fiber drawing techniques providing manufacturing economies of scale.

Other features and advantages of the present invention will be better understood upon reading of preferred embodiments thereof with reference to the appended drawings.

DESCRIPTION OF PREFERRED EMBODIMENTS OF THE INVENTION

Figure 1:
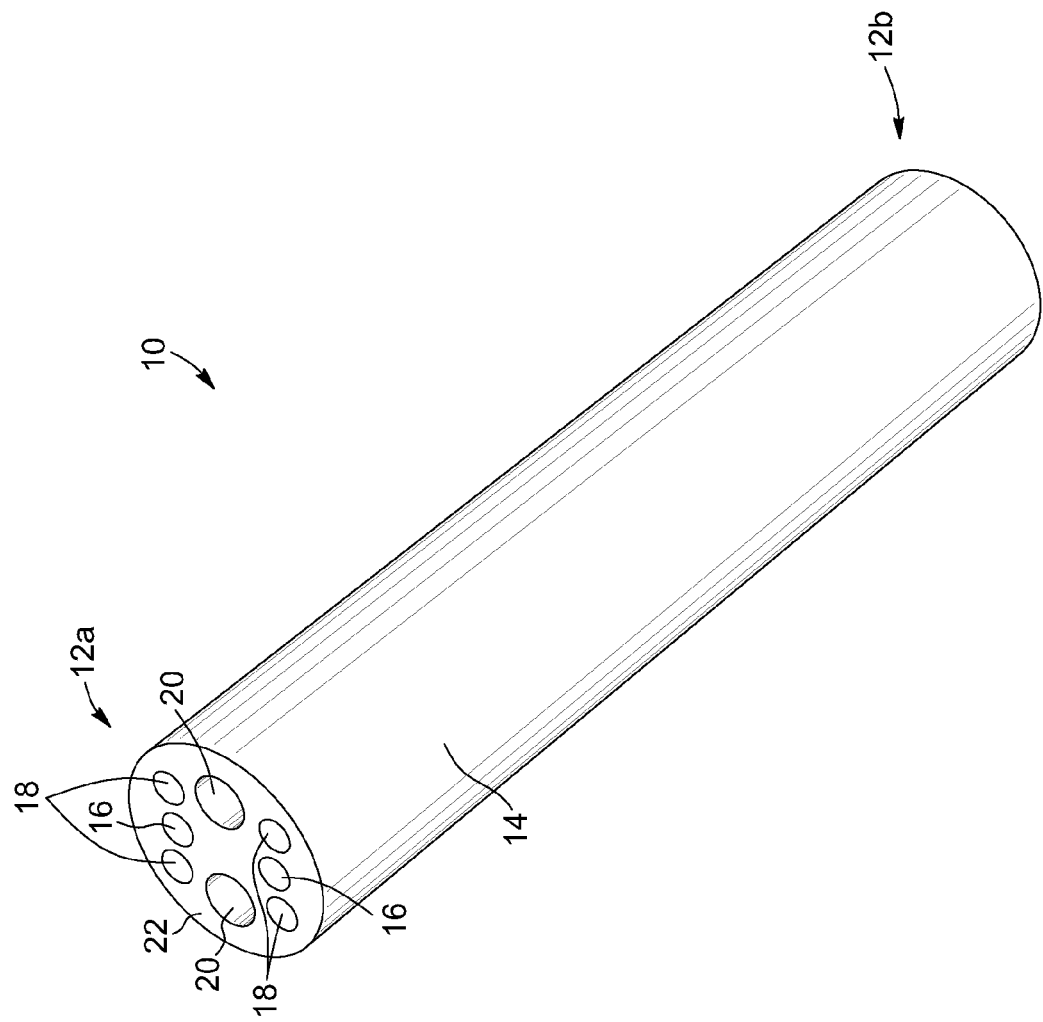
FIG. 1 is a schematic perspective view of an optogenetic probe according to an embodiment of the invention.

In the following description, similar features in the drawings have been given similar reference numerals and in order to weigh down the figures, some elements may not be referred to on some figures if they were already identified in preceding figures. It should also be understood herein that the elements of the drawings are not necessarily drawn to scale and that the emphasis is instead being placed upon clearly illustrating the elements and structures of the present embodiments.

It is also to be understood that certain descriptions of the present invention have been simplified to illustrate only those elements and limitations that are relevant to a clear understanding of the present invention, while eliminating, for purposes of clarity, other elements. Those of ordinary skill in the art, upon considering the present description of the invention, will recognize that other elements and/or limitations may be desirable in order to implement some embodiments of the present invention. However, because such other elements and/or limitations may be readily ascertained by one of ordinary skill upon considering the present description, and are not necessary for a complete understanding of the present invention, a discussion of such elements and limitations is not provided herein.

The present invention generally relates to an optogenetic probe, an optogenetic system, and a method for fabricating an optogenetic probe. Embodiments of the present invention may be particularly useful in any optogenetic applications where it is desired to provide optical, electrical and fluidic functionalities simultaneously into a single device.

Advantageously, embodiments may provide cell-type-specific (micrometer-scale spatial resolution) and temporally precise (millisecond timescale resolution) minimally invasive optogenetic probes that allow simultaneous optical, electrical and fluidic functionalities through a combination of a plurality of channels for injecting and collecting optical light, for impressing electrical voltage or current, and for delivering fluids within living tissues. Also advantageously, optogenetic probes according to embodiments of the invention may allow for the non-invasive study and control of action potentials in living organisms and for the control of cellular function within intact animals.

Optogenetic Probe

Figure 2:
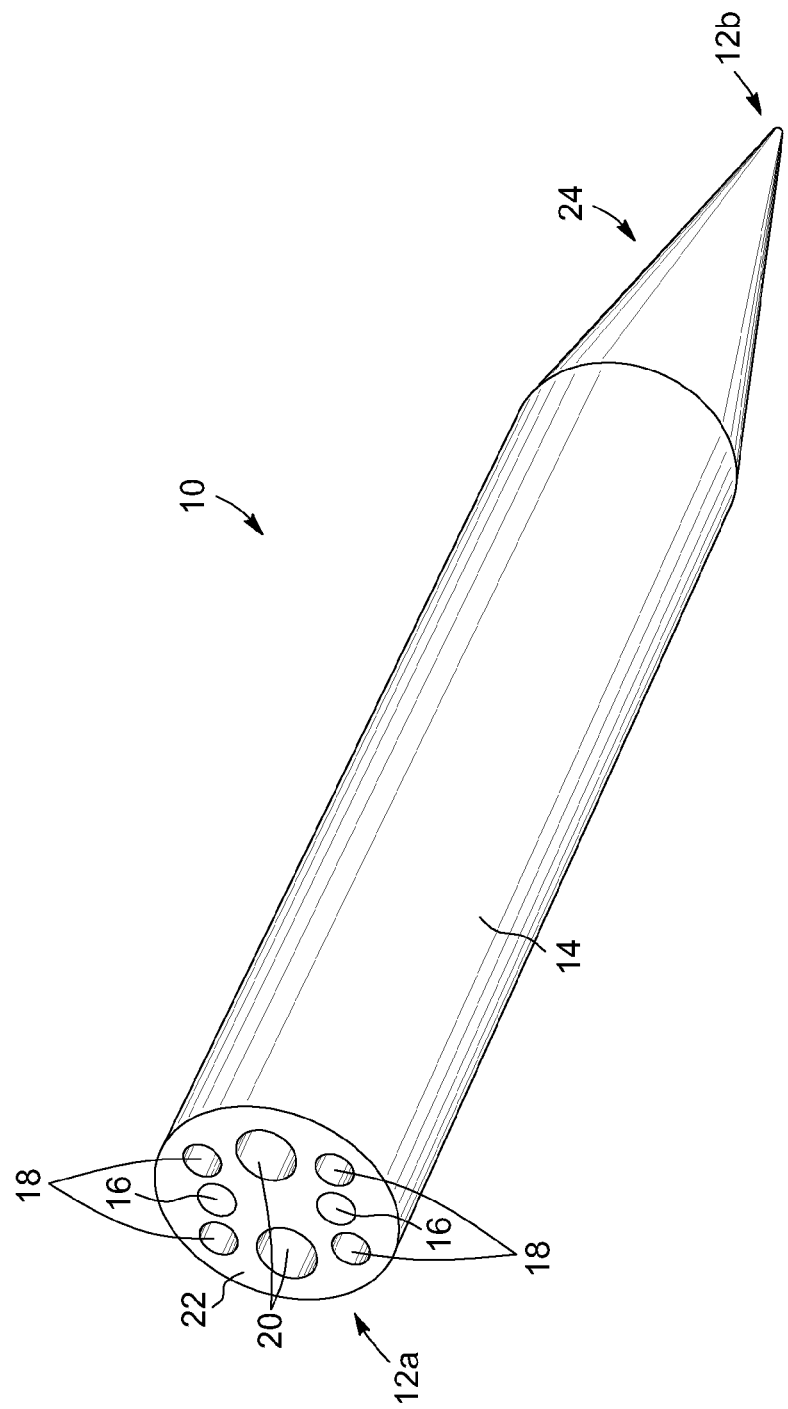
FIG. 2 is a schematic perspective view of an optogenetic probe according to another embodiment of the invention, wherein the distal end of the probe has a tapered shape.

According to an aspect of the invention, there is provided an optogenetic probe 10, exemplary embodiments of which are shown in FIGS. 1 and 2. It is to be noted that for convenience, the optogenetic probe will also be referred to herein simply as a "probe".

In the embodiments shown in FIGS. 1 and 2, the optogenetic probe 10 includes a proximal end 12a and a distal end 12b. As used herein, the term "proximal" refers to the end of the probe closer to the means described below for injecting and collecting light, electrical current or voltage, and fluid, while the term "distal" refers to the end of the probe further away these means for injecting and collecting light, electrical energy and fluid. It will also be understood that the proximal end is typically closer to the user or operator of the probe, while the distal end is typically further away from the user and placed near the structure or event to be probed.

Broadly described and as is discussed in greater detail hereinbelow, the optogenetic probe 10 includes an elongated body 14 extending longitudinally between the proximal and distal ends 12a, 12b, at least one optical channel 16 for guiding light along and within the probe 10, at least one electrical channel 18 for conducting electricity along and within the probe 10, and at least one fluidic channel 20 for transporting fluid along and within the probe. Each of the optical 16, electrical 18 and fluidic 20 channels extends longitudinally within the elongated body 14. As used herein, the term "extending longitudinally within the elongated body" is intended to mean that each optical, electrical and fluidic channel extends lengthwise between the proximal and distal ends of the optogenetic probe so as to be enclosed inside or surrounded by the elongated body.

The overall shape of the optogenetic probe 10 is generally defined by that of the elongated body 14 and may be generally cylindrical, conical, tapered or any other elongated shape. The shape of the cross-section 22 of the probe 10 is also generally defined by that of the elongated body 14 and may assume a variety of shapes such as, for example, circular, elliptical, or any other appropriate shape. In this regard, it will be understood by one of ordinary skill in the art that the optogenetic probe 10 according to this aspect of the present invention is not limited to a particular shape. The length of probe 10, that is, the longitudinal extent between the proximal and distal ends 12a, 12b, may for example be in the range from 1 to 20 centimeters (cm). In some embodiments, the diameter of the proximal end 12a of the probe 10 may be in the range from 100 to 2000 micrometers (μm), while the diameter of the distal end 12b may be in the range from 1 to 200 μm. Of course, it will be understood that these dimensions are given for illustrative purposes only and should not be construed as limiting.

In embodiments of the invention, the distal end 12b of the probe 10 can be inserted into a living organism and may, but need not, have a shape different than the proximal end 12a of the probe 10. For example, in the embodiment shown in FIG. 2, the optogenetic probe 10 has a frusto-conical or otherwise narrowing distal portion 24 that tapers toward the distal end 12b. The tapering of the probe cross-section can be achieved by various methods including, without being limited to, thermal drawing, chemical etching or mechanical embossing of the probe. It will be understood that the shape of the optogenetic probe 10 shown in FIG. 2 is provided as an example only, and that the distal portion 24 of the probe 10, if any, may assume a variety of shapes without departing from the scope of the present invention.

Elongated Body

Still referring to FIGS. 1 and 2, the optogenetic probe 10 first includes an elongated body 14 which, as mentioned above, generally defines the overall shape and structure of the probe 10. The elongated body 14 extends longitudinally between the proximal and distal ends 12a, 12b of the optogenetic probe 10 and is made of a body glass material having a refractive index and an electrical conductivity.

As used herein, the term "glass material" generally refers to an amorphous or non-crystalline solid material whose atoms or molecules lack the long-range order characteristic of a crystal. In this regard, it will be understood that the use of the term "glass" is not meant to refer to any specific material. It will also be understood that the term "glass" is intended to cover both materials which are entirely glassy as well as materials which are substantially glassy with a small crystalline phase. As embodiments of the present invention can be used in optogenetic applications, the body glass material is preferably a biocompatible material.

The term "refractive index" refers herein to the ratio of the speed of light traveling in free space to the speed of light traveling in a medium. It will be understood that, as used herein, the terms "light" and "optical" refer to electromagnetic radiation in any appropriate region of the electromagnetic spectrum and are not limited to visible light, as discussed in greater detail below.

As used herein, the terms "electrical conductivity" and "electrical conductance" refer to a quantity that reflects the ability of a material to conduct or transmit an electrical current. Electrical conductivity can be expressed in siemens per meter ($S \cdot m^{-1}$) in SI unit and is meant to encompass both direct current (DC) and alternating current (AC) electrical conductivity. Electrical conductance can be expressed in siemens (S) in SI unit and is meant to encompass both direct current (DC) and alternating current (AC) electrical conductance.

Various glass compositions can be used for the body glass material making up the elongated body. For example, as will be described in greater detail below, the elongated body 14 of the probe 10 may, without limitation, be a glass compound selected from the group consisting of a phosphate glass of formula $AgPO_3$—$WO_3$, a tellurium oxide glass of formula $TeO_2$, a germanium oxide glass of formula $GeO_2$—$PbO$, a gallium oxide glass of formula $Ga_2O_3$, an antimony oxide glass of formula $Sb_2O_3$, $SiO_2$, a glass of formula $NaPO_3$—$PbF_2$, a glass of formula $NaPO_3$—$WO_3$, a glass of formula $NaPO_3$—$Nb_2O_5$ and a combination thereof.

Optical Channels

Still referring to FIGS. 1 and 2, the optogenetic probe 10 also includes at least one optical channel 16 extending longitudinally within the elongated body 14. For example, in the embodiments shown in FIGS. 1 and 2, the optogenetic probe 10 includes two optical channels 16, but in other embodiments the one or more optical channels may differ in number without departing from the scope of the invention. Each optical channel 16 includes an optical channel glass material having a refractive index larger than the refractive index of the body glass material, so as to guide light therealong.

It will be understood that the material composition of the body glass material of the elongated body 14 and the optical channel glass material of each optical channel 16 are selected so that light can be guided inside the optical channels 16 by total internal reflection. As will be understood by one of ordinary skill in the art, this can be achieved when the optical channel glass material has a refractive index larger than the refractive index of the body glass material. For example, in some embodiments, the refractive indices of the body glass material and optical channel glass material may selected so that the numerical aperture of each optical channels is at least 0.10 or higher, preferably 0.20 or higher, thereby providing efficient guiding of light along each optical channel.

Each optical channel 16 preferably extends continuously from the proximal end 12a to the distal end 12b of the optogenetic probe 10, and may range from about 1 μm to about 500 μm in diameter. Moreover, each optical channel 16 may transmit light along the length thereof with a transmission efficiency of at least 50%, preferably in the wavelength range from 300 to 4000 nanometers (nm), which corresponds to a spectral region extending from the near ultraviolet to the mid-infrared. Of course, one of ordinary skill in the art will recognize that the parameters for the optical channels 16 given above are provided for exemplary purposes only and should not be construed as limiting.

As for the body glass material making up the elongated body, various glass compositions can be used for the optical channel glass material. Again, as mentioned above, the optical channel glass material of each optical channel is selected so as to have a refractive index larger than that of the body glass material of the elongated body. The optical channel glass material may also have a glass softening temperature and a coefficient of thermal expansion which are respectively similar to the glass softening temperature and coefficient of thermal expansion of the body glass material. In one embodiment, the term "similar" means that glass softening temperatures of the body glass material and the optical channel glass material differs from each other by less than a predetermined amount, for example by less than 30 degrees Celsius, and that the coefficients of thermal expansion of the body glass material and the optical channel glass material differs from each other by less than a predetermined amount, for example by less than 3 ppm per degree Celsius.

Non-limiting exemplary glass compositions for the optical channel glass material are provided below. It is to be noted that, for each glass composition, the symbol "A" refers to an additive. The role of the additive "A" may be to increase the refractive index of the optical channel glass material compared to the surrounding body glass material. Exemplary compositions for the additive "A" are described in greater detail below.

In some embodiments, the optical channel glass material may be a glass compound selected from the group consisting of phosphate glass $AgPO_3$—$WO_3$ having a molar constituent optimized to form a stable glass with a composition defined as follows:

$(AgPO_3)_{1-x-y}(WO_3)_x A_y$, preferably where $x \leq 0.30$ and $y \leq 0.70$, further preferably with $x \leq 0.20$, and still further preferably with $x=0.05$.

In other embodiments, the optical channel glass material may be a glass compound selected from the group consisting of tellurium oxide glass $TeO_2$ having a molar constituent optimized to form a stable glass with a composition defined as follows:

$(TeO_2)_{1-x} A_x$, preferably where $x \leq 0.30$, further preferably with $0.05 \leq x \leq 0.20$.

In other embodiments, the optical channel glass material may be a tellurium oxide glass compound corresponding to the "TNZ glass" with a composition of formula $(TeO_2)_{1-x}(Na_2O)_{x-y}(ZnO)_y$, where $x=0.20$ and $y=0.10$.

In other embodiments, the optical channel glass material may be a tellurium oxide glass compound corresponding to the "TBZ glass" with a composition of formula $(TeO_2)_{1-x}(Bi_2O_3)_{x-y}(ZnO)_y$, where $x=0.20$ and $y=0.15$.

In other embodiments, the optical channel glass material may be a glass compound selected from the group consisting of germanium oxide glass $GeO_2$—$PbO$ having a molar constituent optimized to form a stable glass with a composition defined as follows:

$(GeO_2)_{1-x-y}(PbO)_xA_y$, preferably where $x \leq 0.60$ and $y \leq 0.40$, further preferably where $0.30 \leq x \leq 0.50$.

In other embodiments, the optical channel glass material may be a glass compound selected from the group consisting of gallium oxide glass $Ga_2O_3$ having a molar constituent optimized to form a stable glass with a composition defined as follows:

$(Ga_2O_3)_{1-x}A_x$, preferably where $x \leq 0.25$, further preferably where $0.05 \leq x \leq 0.20$.

In other embodiments, the optical channel glass material may be a glass compound selected from the group consisting of antimony oxide glass $Sb_2O_3$ having a molar constituent optimized to form a stable glass with a composition defined as follows:

$(Sb_2O_3)_{1-x}A_x$, preferably where $x \leq 0.25$, further preferably where $0.05 \leq x \leq 0.20$.

In other embodiments, the optical channel glass material may be a glass compound selected from the group consisting of silicon oxide glass $SiO_2$ having a molar constituent optimized to form a stable glass with a composition defined as follows:

$(SiO_2)_{1-x}A_x$, preferably where $x \leq 0.40$, further preferable where $0.05 \leq x \leq 0.30$.

In other embodiments, the optical channel glass material may be a glass compound selected from the group consisting of glass of formula $NaPO_3$—$PbF_2$ having a molar constituent optimized to form a stable glass with a composition defined as follows:

$(NaPO_3)_{1-x-y}(PbF_2)_xA_y$, preferably where $x \leq 0.30$ and $y \leq 0.50$, further preferably where $0.05 \leq x \leq 0.20$.

In other embodiments, the optical channel glass material may be a glass compound selected from the group consisting of glass of formula $NaPO_3$—$WO_3$ having a molar constituent optimized to form a stable glass with a composition defined as follows:

$(NaPO_3)_{1-x-y}(WO_3)_xA_y$, preferably where $x \leq 0.30$ and $y \leq 0.50$, further preferable with $0.05 \leq x \leq 0.20$.

In other embodiments, the optical channel glass material may be a glass compound selected from the group consisting of germanium oxide glass $NaPO_3$—$Nb_2O_5$ having a molar constituent optimized to form a stable glass with a composition defined as follows:

$(NaPO_3)_{1-x-y}(Nb_2O_5)_xA_y$, preferably where $x \leq 0.30$ and $y \leq 0.50$, further preferably where $0.02 \leq x \leq 0.20$.

It will be understood that mixtures of the glass compounds listed above could be used in some embodiments. It will also be understood that in some embodiments, the optical channel glass material need not be based on the same glass compound as the body glass material, as the optical channel glass material of each optical channel has a refractive index larger than that of the body glass material of the elongated body. For example, in one embodiment where the body glass material would a phosphate glass of formula $AgPO_3$—$WO_3$, the optical channel glass material need not also be a phosphate glass of formula $(AgPO_3)_{1-x-y}(WO_3)_xA_y$, but could be embodied by any other suitable glass material that may have a glass softening temperature and a coefficient of thermal expansion which are respectively similar to the glass softening temperature and coefficient of thermal expansion of the body glass material.

Electrical Channels

Still referring to FIGS. 1 and 2, the optogenetic probe 10 also includes at least one electrical channel 18 extending longitudinally within the elongated body 14. For example, in the embodiments shown in FIGS. 1 and 2, the optogenetic probe 10 includes four electrical channels 18, but in other embodiments the one or more electrical channels may differ in number without departing from the scope of the invention. Each electrical channel 18 includes an electrical channel structure having an electrical conductivity larger than the electrical conductivity of the body glass material, so as to conduct electricity therealong.

It will be understood that the higher electrical conductivity of the electrical channel structure compared to the electrical conductivity of the body glass material can provide efficient electrical current conduction along each electrical channel 18. For example, in some embodiments, the electrical channel structure may be selected so as to provide electrical channels 18 exhibiting an electrical conductance of 1 micro-siemen or higher, preferably 1 milli-siemen or higher. As mentioned above with regard to the elongated body 14, the electrical conductivity of each electrical channel 18 can be either a DC or an AC electrical conductivity. Each electrical channel 18 preferably extends continuously from the proximal end 12a to the distal end 12b of the optogenetic probe 10, and may range from about 1 μm to about 200 μm in diameter, preferably 50 μm in diameter. It will be understood that these parameters for the electrical channels 18 are provided for exemplary purposes only and should not be construed as limiting.

In some embodiments, such as in FIG. 1, the electrical channel structure of each electrical channel 18 may include an electrical channel glass material of formula $(AgPO_3)_{1-u-v}(WO_3)_uM_v$, preferably where $u \leq 0.30$, $v \leq 0.70$, and where "M" is an additive, preferably a metal oxide such as, for example, AgI. In these embodiments, the glass body material may be a phosphate glass of formula $AgPO_3$—$WO_3$, such that the role of the additive "M" may be to increase the electrical conductivity of the electrical channel glass material compared to the surrounding $AgPO_3$—$WO_3$ body glass material. Other exemplary compositions for the additive "M" are given further below.

Alternatively, in other embodiments, such as in FIG. 2, the electrical channel structure of each electrical channel 18 may include a hollow electrical channel coated with a thin metallic layer, preferably a metallic silver layer, whose electrical conductivity is larger than the electrical conductivity of the surrounding body glass material of the elongated body 14.

Fluidic Channels

Still referring to FIGS. 1 and 2, the optogenetic probe 10 further includes at least one fluidic channel 20 extending longitudinally within the elongated body 14 and adapted for transporting fluid therealong. In the embodiments shown in FIGS. 1 and 2, the optogenetic probe 10 includes two fluidic channels 20, but in other embodiments the one or more fluidic channels may differ in number without departing from the scope of the invention. The one or more fluidic channels 20 may be embodied by hollow cavities, or empty holes, defined through the elongated body 14. In addition, each fluidic channel 20 preferably extends continuously from the proximal end 12a to the distal end 12b of the probe 10, and may range from about 1 μm to 300 μm in diameter. Furthermore, the one or more fluidic channels 20 may be adapted in size and shape to transport any desired fluids such as, for example, aqueous fluids, solvent-based fluids, organic fluids or other non-aqueous fluids, preferably with a dynamic viscosity in the range from about 0.1 to 10 centipoises (cP). The one or more fluidic channels may have the capacity to transport fluids from the proximal end 12a to the distal end 12b of the probe, or vice versa, with either a continuous or alternating flow of 1 μL/min or higher. Of course, these parameters for the fluidic channels 20 are given for exemplary purposes only and should not be construed as limiting.

Exemplary Embodiments for the Optogenetic Probe

As discussed above, the optogenetic probe according to embodiments of the invention generally includes an elongated body made of a body glass material and at least one optical channel, electrical channel and fluidic channel, each extending longitudinally within the elongated body. Exemplary and non-limiting material compositions for the body and channels of the optogenetic probe according to embodiments of the invention are provided below.

Each optical channel includes an optical channel glass material glass material having a refractive index larger than the refractive index of the body glass material. In some embodiments, the optical channel glass material may include an additive "A" that contributes, inter alia, to increase the refractive index of the optical channel glass material above that of the body glass material. Furthermore, each electrical channel includes an electrical channel structure having an electrical conductivity larger than the electrical conductivity of the body glass material. In some embodiments, the electrical channel structure may include an electrical channel glass material, while in other embodiments the electrical channel structure may include a hollow electrical channel coated with an electrically conducting layer. In some embodiments, the electrical channel glass material may include an additive "M" that contributes, inter alia, to increase the electrical conductivity of the electrical channel glass material above that of the body glass material.

Various materials can be used as the glass additive "A" and "M" respectively incorporated into the optical and electrical channel glass materials. For example, the additives "A" and "M" may be, without being limited to, selected from the group consisting of:

- a transition metal oxide such as, for example, ZnO or $WO_3$ or $Nb_2O_5$ or $Ti_3O_5$ or $Zr_3O_5$ or $Ag_2O$ or $AgNO_3$ or $V_2O_5$ or $Cr_2O_3$ or $Cu_2O$, or any other transition metal oxide, or a mixture thereof;
- an alkali metal oxide such as, for example, $Li_2O$ or $Na_2O$ or $K_2O$ or $NaPO_3$, or any other alkali metal oxide, or a mixture thereof;
- a pnictogen metal oxide such as, for example, $P_2O_5$ or $Sb_2O_3$ or $Bi_2O_3$, or any other pnictogen metal oxide, or a mixture thereof;
- an oxide of the elements of group 13 of the periodic table such as, for example, $In_2O_3$ or $Ga_2O_3$, or any other group 13 oxide, or a mixture thereof;
- an oxide of the elements of group 14 of the periodic table, such as, for example, $SiO_2$ or $GeO_2$ or $SnO_2$, or any other group 14 oxide, or a mixture thereof;
- an halogen compound such as, for example, AgI or $PbF_2$ or AgCl, or any other halogen compound, or a mixture thereof; and
- a mixture of several of these oxides and compounds.

In other embodiments, the glass additives "A" and "M" may also consist of dispersed nanoparticles in the glass, such as carbon nanotubes or metallic nanoparticles.

It will be understood, however, that the additives "A" and "M" are selected according to the desired optical and electrical properties modification of the resulting glass compounds, and are not limited to the specific oxides, compounds or structures listed above.

The glass additives "A" and "M" may be incorporated into the compositions of the optical and electrical channel glass materials, such as those listed above in the sections "Optical channels" and "Electrical channels", respectively. More specifically, glass additives may be mixed to glass materials selected from the group consisting of $AgPO_3$—$WO_3$ glass compounds, $TeO_2$ glass compound, $GeO_2$—PbO glass compounds, $Ga_2O_3$ glass compounds, $Sb_2O_3$ glass compounds, $SiO_2$ glass compounds, $NaPO_3$—$PbF_2$ glass compounds, $NaPO_3$—$WO_3$ glass compounds, $NaPO_3$—$Nb_2O_5$ glass compounds, and mixtures thereof.

The additives "A" and "M" may be employed in order to functionalize the physical properties of the optical and electrical channel glass materials according to desired optical or electrical properties for the one or more optical and electrical channels, to improve their manufacturability, or to improve their glass stability. Glass functionalization can provide optical and electrical functionalization for the optogenetic probe according to embodiments of the invention. This functionalization scheme is preferably applied to glass materials that are compatible for fiber co-drawing, as will be described in greater detail below.

For example, in some embodiments, the additives "A" and "M" may contribute to increase the refractive index of the optical channel glass material to provide the optical channel or channels a numerical aperture of at least 0.10, or to increase the electrical conductivity of the electrical channel glass material to provide electrical channel or channels with an electrical conductance of at least 1 micro-siemen, or to adjust the softening temperature of the glass materials for viscosity matching purposes during fiber drawing, or to adjust the coefficient of thermal expansion of the glass materials to improve the materials and mechanical stability of the probe.

For example, in some embodiments, the optogenetic probe may have the following composition: a body glass material of formula $AgPO_3$—$WO_3$; an optically-transparent optical channel glass material of formula $(AgPO_3)_{1-x-y}(WO_3)_xA_y$; and an electrically-conductive electrical channel glass material of formula $(AgPO_3)_{1-u-v}(WO_3)_uM_v$.

In such embodiments, $AgPO_3$ forms a mesh-like atomic structure, which imparts glass stability and optical transparency, while tungsten oxide $WO_3$ promotes electrical conductivity. Furthermore, depending on the nature of the additives "A" and "M", different characteristics may be imparted to the optical and electrical channel glass materials. For example, transition metal oxides mixed in small amount to the phosphate glass $AgPO_3$—$WO_3$ may impart characteristics such as high electrical conductivity, high refractive index, reduced melting temperature, and decreased temperature of the viscous glass. On the other hand, alkali metal oxides mixed in small amount to this phosphate glass may impart characteristics such as an improved resistance of the glass to loss of transparency, decreased yield point temperature and liquid phase temperature, and improved high-temperature melting properties of the glass. Moreover, pnictogen metal oxides mixed in small amount to this phosphate glass may impart characteristics such as refining and homogenizing the glass.

In other embodiments, as mentioned above, rather than being embodied by an electrical channel glass material incorporating an additive "M", the electrical channel structure of each electrical channel may include a hollow electrical channel coated with an electrically conducting layer. The electrically conducting layer may be a thin metallic layer, preferably silver, having a higher electrical conductivity than the surrounding body glass material of the elongated body. For example, in one embodiment, the electrical conductivity of the thin metallic layer can yield electrical channels having an electrical conductance of 1 milli-siemen or more.

In some embodiments, each hollow electrical channel may be coated with a thin metallic silver layer according to Tollen's chemical reaction, which is discussed in greater detail below. The Tollen's reaction may be applicable to optogenetic probes fabricated from a wide variety of optically-transparent glass compounds that may not have sufficient intrinsic electrical conductivity for optogenetic applications where high electrical conductivities are desired or required. Such compounds may be selected from the glass compositions listed above in the section "Optical channels" and based on optically-transparent glass materials selected, for example, from the group consisting of phosphate glass $AgPO_3$—$WO_3$, tellurium oxide glass $TeO_2$, germanium oxide glass $GeO_2$.PbO, gallium oxide glass $Ga_2O_3$, antimony oxide glass $Sb_2O_3$, silicon oxide glass $SiO_2$, $NaPO_3$—$PbF_2$ glass and of $NaPO_3$—$WO_3$ glass.

Specific embodiments of the optogenetic probe, including the material composition and structure of the elongated body and the one or more optical, electrical and fluidic channels are exemplified below. Of course, these embodiments are provided for illustrative purposes and should not be construed as limiting the scope of the present invention.

In one embodiment, the elongated body and the channels of the probe are selected from, but not restricted to, the following material compositions:

Elongated body: $(AgPO_3)_{1-x}(WO_3)_x$, with $x=0.00$;
Optical channel(s): $(AgPO_3)_{1-x}(WO_3)_x$, with $x=0.02$;
Electrical channel(s): $(AgPO_3)_{1-u-v}(WO_3)_u(AgI)_v$, with $u=0.05$, $v=0.20$; and
Fluidic channel(s): Hollow channels.

In one embodiment, the glass compounds are selected from, but not restricted to, the following material compositions:

Elongated body: $(AgPO_3)_{1-x}(WO_3)_x$, with $x=0.00$;
Optical channel(s): $(AgPO_3)_{1-x-y}(WO_3)_x(AgI)_y$, with $x=0.02$, $y=0.10$;
Electrical channel(s): $(AgPO_3)_{1-x-y}(WO_3)_x(AgI)_y$, with $x=0.08$, $y=0.45$; and
Fluidic channel(s): Hollow channels.

In one embodiment, the glass compounds are selected from, but not restricted to, the following material compositions:

Elongated body: $(AgPO_3)_{1-x}(WO_3)_x$, with $x=0.00$;
Optical channel(s): $(AgPO_3)_{1-x}(WO_3)_x$, with $x=0.02$;
Electrical channel(s): Silver-coated hollow channels using Tollen's reaction; and
Fluidic channel(s): Hollow channels.

In one embodiment, the glass compounds are selected from, but not restricted to, the following material compositions:

Elongated body: $(NaPO_3)_{1-x}(Nb_2O_5)_x$, with $x=0.00$;
Optical channel(s): $(NaPO_3)_{1-x}(Nb_2O_5)_x$, with $x=0.02$;
Electrical channel(s): $(AgPO_3)_{1-u-v}(WO_3)_u(AgI)_v$, with $u=0.30$, $v=0.45$; and
Fluidic channel(s): Hollow channels.

In one embodiment, the glass compounds are selected from, but not restricted to, the following material compositions:

Elongated body: $(NaPO_3)_{1-x}(Nb_2O_5)_x$, with $x=0.00$;
Optical channel(s): $(NaPO_3)_{1-x}(Nb_2O_5)_x$, with $x=0.02$;
Electrical channel(s): Silver-coated hollow channels using Tollen's reaction; and
Fluidic channel(s): Hollow channels.

In one embodiment, the glass compounds are selected from, but not restricted to, the following material compositions:

Elongated body: $TeO_2$;
Optical channel(s): $(TeO_2)_{1-x}A_x$, $A=(Na_2O)_{x-y}(ZnO)_y$, $x=0.20$, $y=0.10$;
Electrical channel(s): Silver-coated hollow channels using Tollen's reaction; and
Fluidic channel(s): Hollow channels.

In one embodiment, the glass compounds are selected from, but not restricted to, the following material compositions:

Elongated body: $(GeO_2)_{1-x}(PbO)_x$, with $x=0.50$, $y=0.50$;
Optical channel(s): $(GeO_2)_{1-x-y}(PbO)_x(Ag_2O)_y$, with $x=0.60$, $y=0.05$;
Electrical channel(s): Silver-coated hollow channels using Tollen's reaction; and
Fluidic channel(s): Hollow channels.

In one embodiment, the glass compounds are selected from, but not restricted to, the following material compositions:

Elongated body: $(NaPO_3)_{1-x}(WO_3)_x$, with $x=0.00$;
Optical channel(s): $(NaPO_3)_{1-x}(WO_3)_x$, with $x=0.05$;
Electrical channel(s): $(AgPO_3)_{1-u-v}(WO_3)_u(AgI)_v$, with $u=0.30$, $v=0.45$; and
Fluidic channel(s): Hollow channels.

In one embodiment, the glass compounds are selected from, but not restricted to, the following material compositions:

Elongated body: $(NaPO_3)_{1-x}(PbF_2)_x$, with $x=0.00$;
Optical channel(s): $(NaPO_3)_{1-x}(PbF_2)_x$, with $x=0.05$;
Electrical channel(s): $(AgPO_3)_{1-u-v}(WO_3)_u(AgI)_v$, with $u=0.30$, $v=0.45$; and
Fluidic channel(s): Hollow channels.

In one embodiment, the glass compounds are selected from, but not restricted to, the following material compositions:

Elongated body: $SiO_2$;
Optical channel(s): $(SiO_2)_{1-y-z}(GeO_2)_y(P_2O_5)_z$, with $y=0.25$, $z=0.02$;
Electrical channel(s): Silver-coated hollow channels using Tollen's reaction; and
Fluidic channel(s): Hollow channels.

In one embodiment, the glass compounds are selected from, but not restricted to, the following material compositions:

Elongated body: $SiO_2$;
Optical channel(s): $(SiO_2)_{1-x}(P_2O_5)_x$, with $x=0.20$;
Electrical channel(s): Silver-coated hollow channels using Tollen's reaction; and
Fluidic channel(s): Hollow channels.

In one embodiment, the glass compounds are selected from, but not restricted to, the following material compositions:

Elongated body: $SiO_2$;
Optical channel(s): $(SiO_2)_{1-x}(GeO_2)_x$, with $x=0.27$;
Electrical channel(s): Silver-coated hollow channels using Tollen's reaction; and
Fluidic channel(s): Hollow channels.

Figure 3:
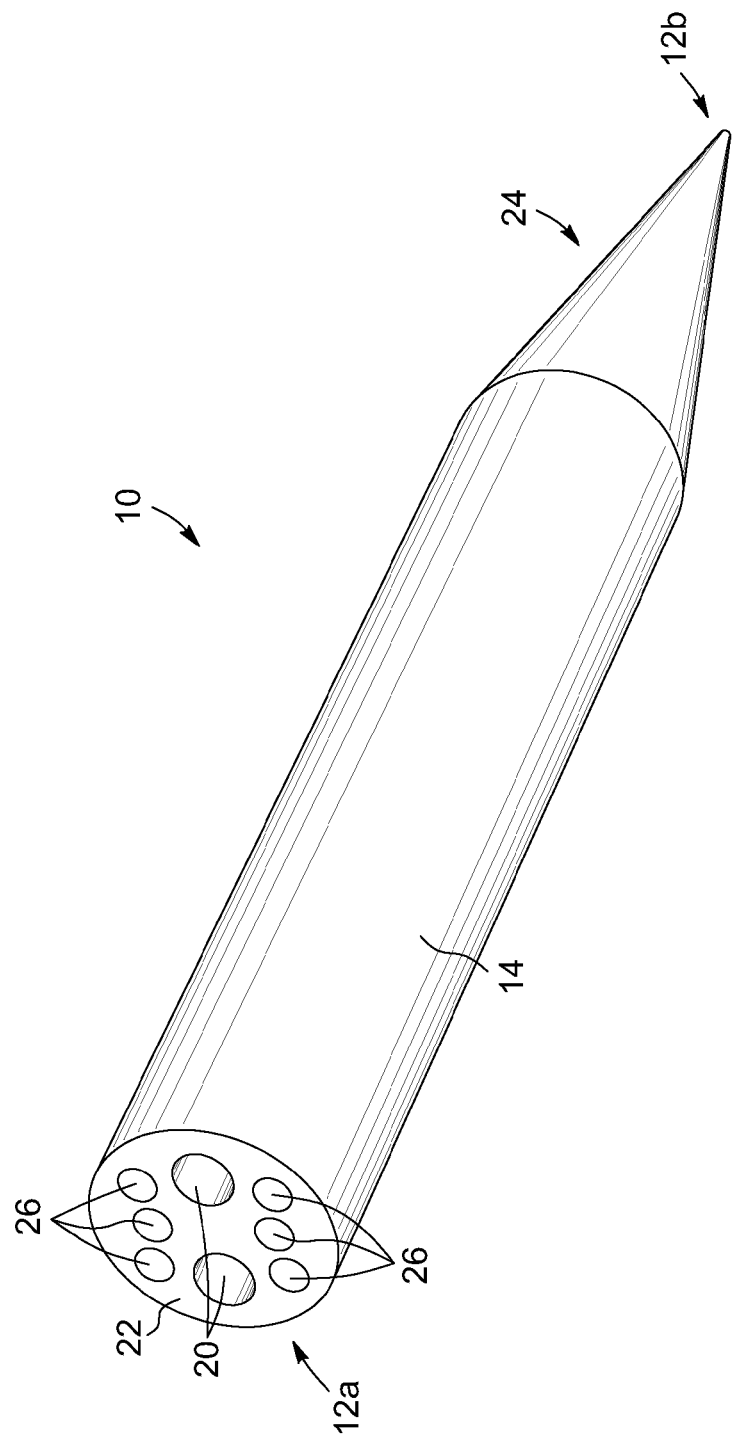
FIG. 3 is a schematic perspective view of an optogenetic probe according to another embodiment of the invention, wherein the probe includes opto-electrical channels simultaneously defining the optical and electrical channels.

Referring to FIG. 3, in some embodiments, glass additives mixed to the optical and electrical channel glass materials may impart both a high electrical conductivity and a high refractive index. As a result, in some of these embodiments, the optogenetic probe 10 such as that shown in FIG. 3 may include one or more opto-electrical channels 26 simultaneously defining one of the at least one optical channel and one of the at least one electrical channel. Each opto-electrical channel 26 thereby combines both optical transmission and electrical conduction. In other words, the optical and electrical channels of the probe 10 shown in FIG. 3 coincide to or are integrated into a same channel having dual optical and electrical functionalities. Such embodiments may result in a simpler configuration for the cross-section 22 of the probe 10.

For example, in an embodiment, the opto-electrical channel 26 may include an optically-transparent and electrically-conductive glass material of formula $(AgPO_3)_{1-x-y}(WO_3)_x(AgI)_y$, where x=0.05 and y=0.45. Such an embodiment may exhibit and electrical conductance of about 1 milli-siemen and an optical transmission of more than 50% for a probe having a length of 1 cm.

Referring back to FIGS. 1 and 2, in other embodiments, the one or more electrical channels 18 may be placed proximal to the one or more optical channels 16 in order to provide, for example via electric-field or electrical-current-injection, dynamical opto-electronic effects to the optical channels 16 such as, for example, induced refractive index change, induced optical attenuation. Such opto-electronic effects may be used to dynamically adjust the optical properties of the optical channels 16 including, without being limited to, changes in their refractive index or the absorption coefficient and shifts in their spectral optical response, as the distal end 12b of the optogenetic probe 10 is inserted into a living organism. In some embodiments, refractive Bragg gratings may also be permanently inscribed into the one or more optical channels 16 in order to provide spectral filtering of optical light.

Optogenetic System

Figure 4:
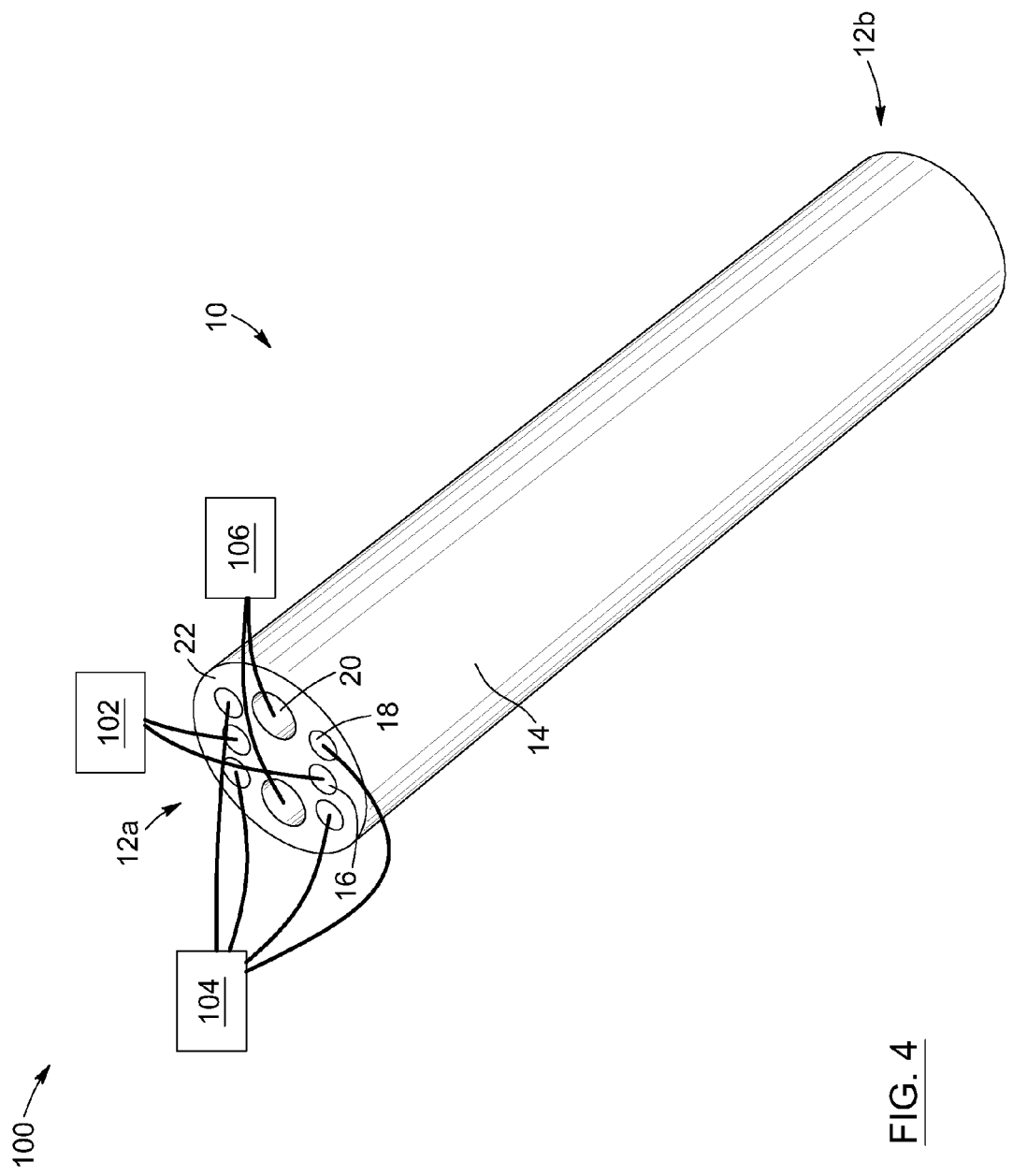
FIG. 4 is a schematic illustration of an optogenetic system according to an embodiment of the invention.

According to another aspect of the invention, there is a provided an optogenetic system 100, an embodiment of which is represented schematically in FIG. 4. The optogenetic system 100 first includes an optogenetic probe 10 such as any of the embodiments described above or variants thereof. The optogenetic system 100 also includes an optical module 102 optically coupled to each optical channel 16 of the optogenetic probe 10, an electrical module 104 electrically coupled to each electrical channel 18 of the optogenetic probe 10, and a fluidic module 106 coupled to each fluidic channel 20 of the optogenetic probe 10. Each of these modules is now described in greater detail below.

The optical module 102 may be located proximate to the one or more optical channels 16 and may include means for injecting and collecting optical light at the proximal end 12a of each optical channel 16. These injecting and collecting means may be embodied by optical fibers, each coupled by precise fiber alignment, at one end thereof, to a corresponding optical channel 16, and, at the other end, to one or more optical sources and optical detectors. More precisely, in one embodiment, precisely aligning the an optical fiber with each optical channel 16 may involve precisely aligning the core of the optical fiber the corresponding optical channel 16, after which the fiber may be attached to the corresponding optical channel 16 using, for example, fiber splicing or any suitable mechanical means including, without limitation, epoxy, glue, ferrules, V-grooves, joints or other fiber attachment devices. As known in the art, exemplary optical sources may include, without being limited to, laser sources such a laser diodes and fiber lasers or light sources such as LEDs, while exemplary optical detectors may include, without being limited to, PIN photodetectors, avalanche photodetectors. Of course, other suitable means for injecting and collecting light at the proximal end 12a of the probe 10 may be employed without departing from the scope of the invention.

The one or more optical sources preferably launch light into the optogenetic probe 10 at the proximal end 12a thereof for propagation along one or more optical channels 16. The light exiting the one or more optical channels 16 can be directed toward a target (e.g. organic tissues) near or surrounding the distal end 12b of the probe 10. Depending on the application, interaction with the target will result in return light generated by any of a variety of optical phenomena such as reflection, scattering, fluorescence and the like. After interaction with the target, the return light is collected by the probe 10 at the distal end 12b and propagates back toward the proximal end 12a along the at least one optical channel 16, where it can be detected by the one or more optical detectors. In the context of optogenetic applications, the light detected by the one or more optical detectors after interaction with the target may consist, for example, of fluorescent light emitted from biological tracers surrounding the distal end 12b of the probe 10. It will be understood that in such applications, the distal end 12b of the optogenetic probe 10 may be inserted into a living organism and is preferably not in physical contact with the means for coupling and detecting light at the proximal end 12a of the probe 10.

The electrical module 104 may also be located proximate to the one or more electrical channels 18. They may include means for impressing electrical voltage and/or current at the proximal end 12a of the probe 10, as well as means for measuring electrical voltage and/or current at the proximal end 12a of the probe 10. Such means may be embodied by electrical sources such as, for example, voltage-current sources, oscilloscopes, function generators, integrated electronic circuits or other suitable means for impressing and measuring DC or AC electrical voltages and currents. In some embodiments, these electrical sources may be electrically connected to the one or more electrical channels 18 by means of small tungsten electrical wires bonded with silver paste each electrical channel 18. In such embodiments, the distal end 12b of the optogenetic probe 10 may be inserted into a living organism and is preferably not in physical contact with the means for impressing electrical voltage and/or current at the proximal end 12a of the probe 10.

As for the optical and electrical modules 102, 104, the fluidic module 106 may be located proximate to the one or more fluidic channels 20 and may include means for delivering fluid back and forth between the proximal end 12a to the distal end 12b of the probe. Such delivering means include syringe-like tubes inserted, at one end thereof, into the one or more fluidic channels 20 and connected, at the other end thereof, to flow-controlled fluidic pumps, microfluidic units, or another suitable means for delivering fluid at controllable flow rates. In such embodiments, the distal end 12b of the probe 10 may be inserted into a living organism and is preferably not in physical contact with the means of delivering fluid from the proximal end 12a to the distal end 12b of the probe.

Method of Fabricating an Optogenetic Probe

Figure 5:
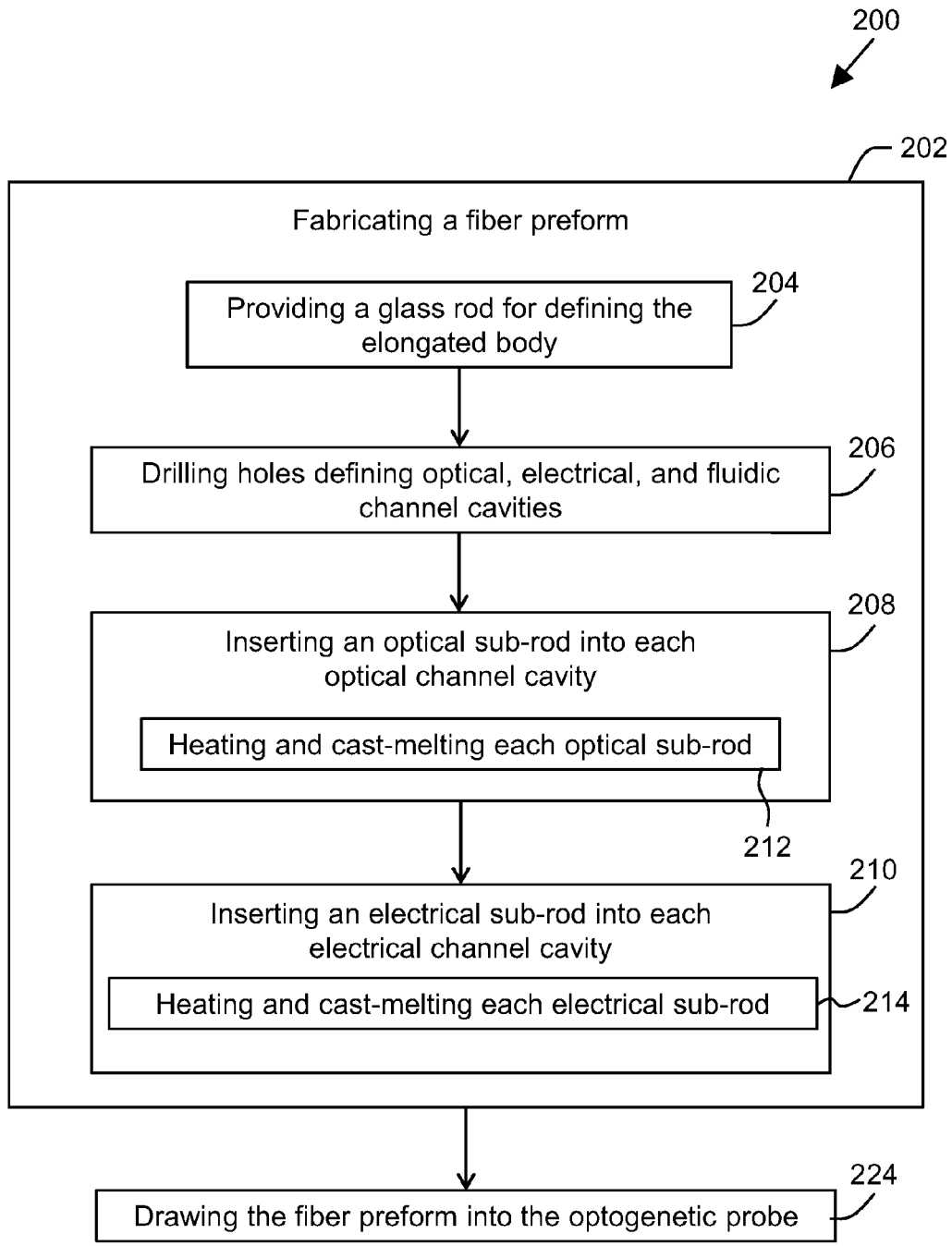
FIG. 5 is flow chart of a method for fabricating an optogenetic probe, in accordance with an embodiment of the invention.

According to a further aspect of the invention, there is provided a method of fabricating an optogenetic probe. FIG. 5 shows a flow chart of an embodiment of the method 200, which could, by way of example, be performed to fabricate an optogenetic probe 10 such as that illustrated in FIGS. 1 to 3.

Broadly described, the method 200 according to this aspect of the invention generally involves the technique of glass fiber drawing. The technique of fiber drawing is well known and can yield extended lengths of highly uniform elongated glass fibers with well-controlled cross-sectional geometries. The cross-sectional geometries may be scaled to micrometer sizes which allow the manufacture of small but robust optogenetic probes that may be inserted in a living organism without significantly disrupting living organic tissues. A technique of drawing glass fibers that has been developed for and is well adapted to the fabrication optogenetic probes according to embodiments of the present invention is described below.

Referring to FIG. 5, the method 200 first includes a step of fabricating 202 a fiber preform that includes an elongated body, at least one optical channel, at least one electrical channel, and at least one fluidic channel. As described above, the elongated body is made of a body glass material having a refractive index, an electrical conductivity, a softening temperature and a coefficient of thermal expansion.

Each optical channel includes an optical channel glass material having a refractive index larger than the refractive index of the body glass material, so as to transmit light therealong. The optical channel glass material also has a glass softening temperature and a coefficient of thermal expansion which respectively similar to the glass softening temperature and coefficient of thermal expansion of the body glass material; so as to enable glass fiber drawing without causing excessive internal material stresses in the glass fiber. In one embodiment, the term "similar" means that glass softening temperatures of the body glass material and the optical channel glass material differs from each other by less than a predetermined amount, for example by less than 30 degrees Celsius, and that the coefficients of thermal expansion of the body glass material and the optical channel glass material differs from each other by less than a predetermined amount, for example by less than 3 ppm per degree Celsius.

Furthermore, each electrical channel includes an electrical channel structure having an electrical conductivity larger than the electrical conductivity of the body glass material, so as to conduct electricity therealong, while each fluidic channel is adapted for transporting fluid therealong.

It will be understood that any preform configuration and preform assembly techniques that employ glass compositions such as $(AgPO_3)_{1-x-y}(WO_3)_xB_y$, or $(TeO_2)_{1-x}B_x$, or $(GeO_2)_{1-x-y}(PbO)_xB_y$, or $(Ga_2O_3)_{1-x}B_x$, or $(Sb_2O_3)_{1-x}B_x$, or $(SiO_2)_{1-x}B_x$, or $(NaPO_3)_{1-x-y}(PbF_2)_xB_y$, or $(NaPO_3)_{1-x-y}(WO_3)_xB_y$, or $(NaPO_3)_{1-x-y}(Nb_2O_5)_xB_y$ that are compatible for fiber co-drawing may be utilized. Here, the symbol "B" refers to an additive and should be understood to encompass both the additive "A" mixed into the optical channel glass material and the additive "M" mixed into the electrical channel glass material, as described above.

As defined herein, fiber co-drawing compatibility is intended to refer to material compositions (x, y, B) having substantially similar glass softening temperatures (e.g. to within a difference of about 30 degrees Celsius) and coefficients of thermal expansion (e.g. to within a difference of about 3 ppm). Such material compositions (x, y, B) can be combined within a same composite fiber preform and drawn into a fiber as a single continuous viscous flow using standard fiber drawing techniques, as described below, wherein all combined glass materials within the composite fiber preform exhibit substantially the same dynamic viscosity of about $10^4$ cP during fiber drawing, thus forming a multi-material composite fiber after cooling and solidification. Fiber co-drawing compatibility can allow obtaining multi-material fibers with matched viscous flow during fiber drawing and matched thermal expansion coefficients after fiber solidification, as described below.

Glass compounds such as those listed above may be prepared using the technique of "melt and casting", which is well known in the art of glass fabrication. According to this technique, glass compounds are processed first by preparing fine powders of the constituents available from high-purity materials suppliers, such as Alfa Aesar (trade name), Sigma-Aldrich (trade name) or Strem Chemicals (trade name). The fine powders are then mixing thoroughly in a high-temperature platinum ($Pt_{95}Au_5$), alumina ($Al_2O_3$) or gold (Au) crucible.

The technique subsequently includes heating the mixed powders to their melting temperature, preferably by using an electrical or inductive furnace, followed by quenching and casting the resulting glass melt. The melting points of the above-mentioned glass compounds are typically between about 1000 to 1100 degrees Celsius for the $(AgPO_3)_x(WO_3)_{1-x}$ glass compound, about 800 degrees Celsius for the $TeO_2$ glass compound, about 1100 degrees Celsius for the $(GeO_2)_{1-x}(PbO)_x$ glass compound, between about 1200 to 1300 degrees Celsius for the $Ga_2O_3$ glass compound, about 1100 degrees Celsius for the $Sb_2O_3$ glass compound, about 2000 degrees Celsius for the $SiO_2$ glass compound, about 1200 degrees Celsius for the $NaPO_3$—$PbF_2$ glass compound, and about 1200 degrees Celsius for the $NaPO_3$—$WO_3$ glass compound.

Once the glass constituents are thoroughly mixed and heated to their melting temperatures, the melts thus obtained may be introduced into quartz tubes for rotational casting and quenching. The technique of rotational casting consists of introducing a glass melt into a heated rotating cylindrical mold, which, by centrifugal force, will distribute the glass melt along the inner periphery of the cylinder in order to form a cylindrical glass tube. The inside-to-outside diameter ratio of the rotational casting is determined according to the volume of glass melt poured into the rotating cylindrical mold. Once the glass melt is cylindrically centrifuged, the rotating cylindrical mold is then cooled down in order to quench/solidify the glass melt into the shape of a tube. In embodiments of the invention, the quench time may be generally less than a minute and preferably less than 15 seconds. In other words, the cooling rate of the glass melt is preferably at least 100 degrees Celsius per second. In some embodiments, the quenched glass may be released from the rotating cylindrical mold and be annealed for about 4 hours at a temperature of 300-400 degrees Celsius to release material stresses.

The glass released from the rotating cylindrical mold has typically the shape of a cylindrical tube or cylindrical rod, which is the basis for the step of fabricating 202 a macroscopic fiber preform. Such a macroscopic fiber preform includes the materials entering the composition of the body and channels of the optogenetic probe, cast and annealed in cylindrical tube shape, and arranged in a macroscopic geometrical configuration. This macroscopic geometrical configuration may, but need not corresponds to the desired geometry of the probe 10, such as that shown in FIGS. 1 to 3. The macroscopic fiber preform typically ranges from about 25 to 50 mm in diameter, which is about 100 times larger than the final diameter of the optogenetic probe.

In one embodiment, the step of fabricating 202 the fiber preform first includes a substep of providing 204 a glass rod extending longitudinally for defining the elongated body of the probe. This may followed by a substep of drilling holes 206 longitudinally through the glass rod for defining at least one optical channel cavity, at least one electrical channel cavity and at least one fluidic channel cavity.

Subsequently, a substep of inserting 208 an optical sub-rod into each optical channel cavity thus defined may be performed so as to define each optical channel of the probe. In these embodiments, the optical sub-rod includes an optical channel glass material having a refractive index larger than the refractive index of the glass body material, so as to transmit light therealong. The optical channel glass material also includes a glass softening temperature and a coefficient of thermal expansion respectively similar to the glass softening temperature and coefficient of thermal expansion of the body glass material. The glass compositions given above may be used for the optical channel glass material, which may include a glass additive "A" to modify its physical properties.

In some embodiments, a substep of inserting 210 an electrical sub-rod into each electrical channel cavity thus defined may be performed, so as to define each electrical channel. In these embodiments, the electrical sub-rod includes an electrical channel glass material having an electrical conductivity larger than the electrical conductivity of the glass body material, so as to conduct electricity therealong. The electrical channel glass material also includes a glass softening temperature and a coefficient of thermal expansion respectively similar to the glass softening temperature and coefficient of thermal expansion of the body glass material. The glass compositions given above may be used for the electrical channel glass material, which may include a glass additive "M" to modify its physical properties.

It will be understood that in these embodiments, the at least one fluidic channel cavity may define the at least one fluidic channel.

In some embodiments, the substep of inserting 208 the one or more optical sub-robs may include heating 212 each optical sub-rod above the glass softening temperature thereof, and melt-casting the same into the hole defining the corresponding optical channel using gravity, vacuum suction, centrifugation, or forced injection. Each optical sub-rod is then solidified within the preform to form the corresponding optical channel. Likewise, the substep of inserting 210 the one or more electrical sub-robs may include heating 214 each electrical sub-rod above the glass softening temperature thereof, and melt-casting the same into the hole defining the corresponding electrical channel using gravity, vacuum suction, centrifugation, or forced injection. Each electrical sub-rod is then solidified within the preform to form the corresponding electrical channel.

In other embodiments, the optical and electrical sub-rods may be heated at the melt state, inserted into the hollow channels using gravity, vacuum suction, centrifugation, or forced injection, and solidified within the preform to form the optical or the electrical channels. Alternatively, the sub-rods may be heated above their glass softening temperatures and melt-casted into the channels using gravity, vacuum suction, centrifugation, or forced injection, and solidified within the preform to form the optical or the electrical channels.

In yet other embodiments, metalorganic chemical vapor deposition (MOCVD) may be used be used to grow thin films of glass, which may include additives "A" or "M", inside the hollow channels to fill the same and form the optical or the electrical channels. MOCVD, as known in the art of fiber preform fabrication, consists of a chemical vapor deposition of materials from the surface reaction of organic compounds or metalorganics and metal hydrides containing the required chemical elements. Alternatively, the preform may be made from various sub-rods assembled together in a hollow tube, each sub-rod either made of the material of the elongated body or that of one of the channels.

Figure 6:
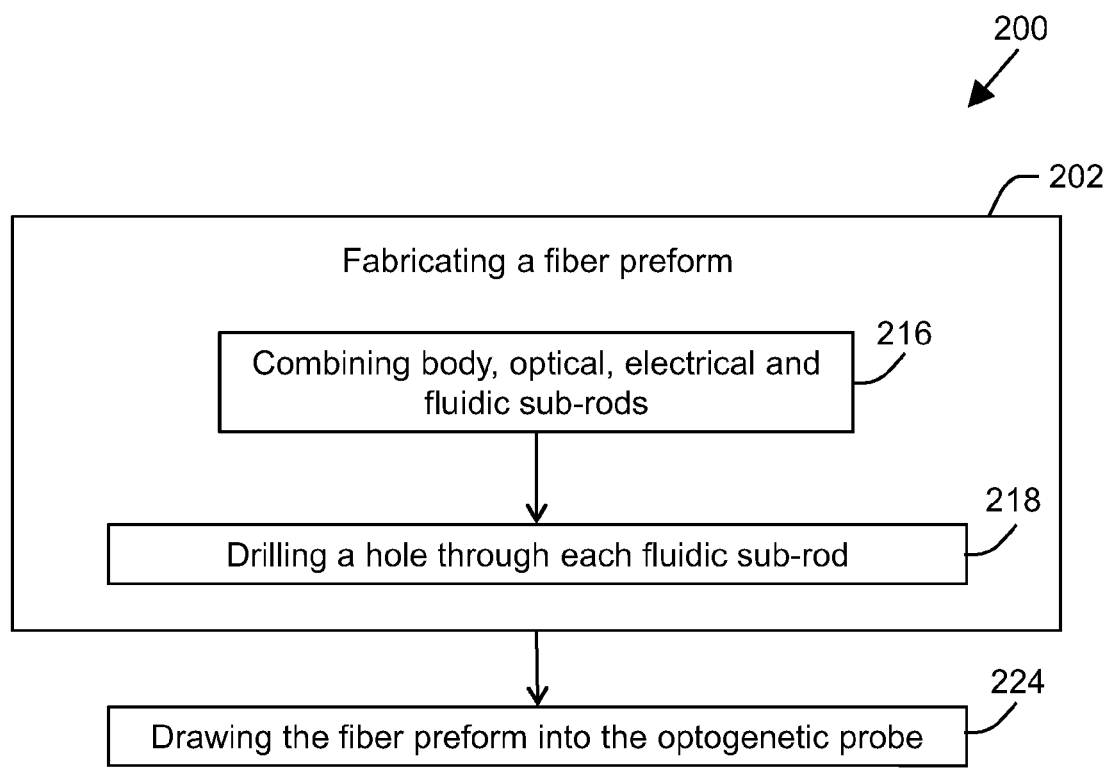
FIG. 6 is flow chart of a method for fabricating an optogenetic probe, in accordance with another embodiment of the invention.

Referring now to FIG. 6, there is shown a flow chart of another embodiment of the method 200, where the step of fabricating 202 the fiber preform includes a substep of combining 216 at least one body sub-rod, at least one optical sub-rod, at least one electrical sub-rod, and at least one fluidic sub-rod, each extending longitudinally. This combination can be followed by a substep of drilling 218 a hole longitudinally through each of the at least one fluidic sub-rod for defining the at least one fluidic channel.

Figure 7:
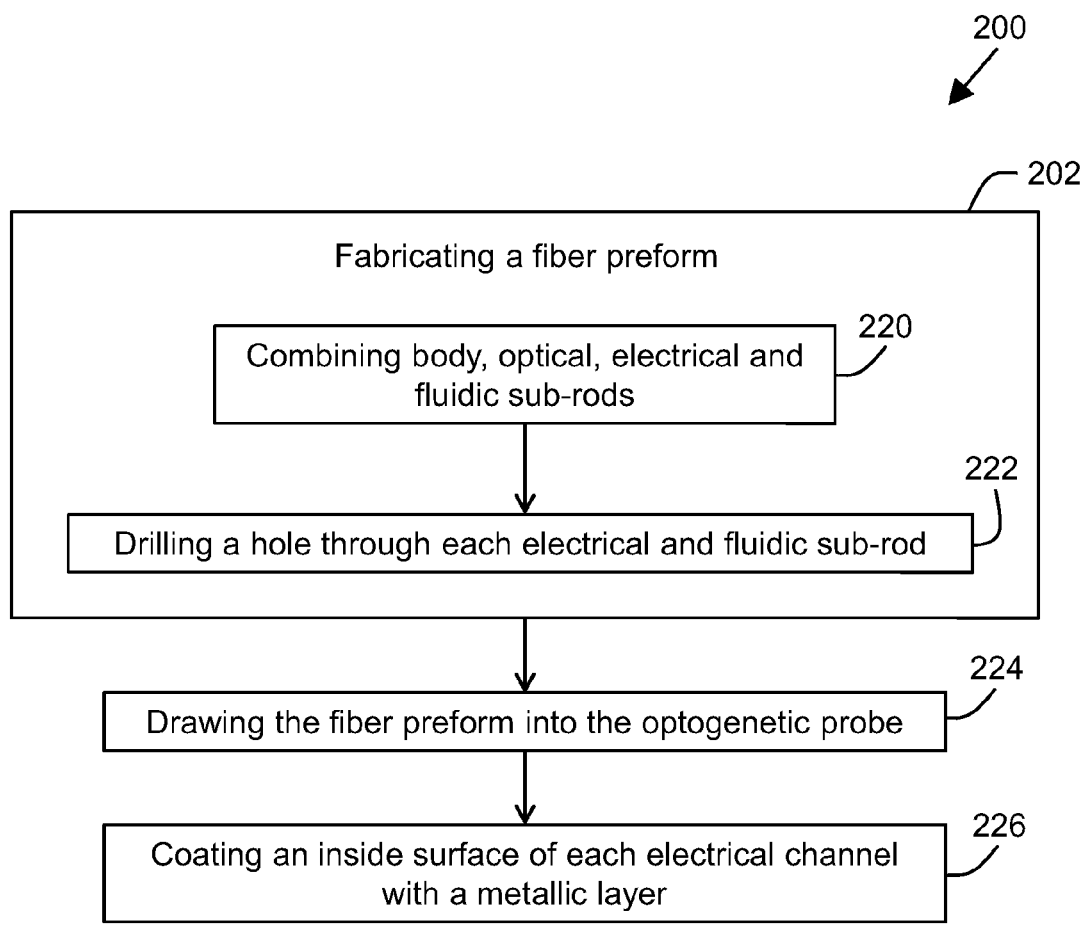
FIG. 7 is flow chart of a method for fabricating an optogenetic probe, in accordance with another embodiment of the invention.

Referring now to FIG. 7, there is shown a flow chart of another embodiment of the method 200, where the step of fabricating 202 the fiber preform includes a substep of combining 220 at least one body sub-rod, at least one optical sub-rod, at least one electrical sub-rod, and at least one fluidic sub-rod, each extending longitudinally. This can be followed by a substep of drilling 222 a hole longitudinally through each of the least one electrical and fluidic sub-rods for defining the at least one electrical channel and the at least one fluidic channel, respectively.

Referring to FIGS. 5 to 7, once assembled, the preform may be consolidated at a temperature proximal to the glass softening temperature of the selected glass materials to smooth the interfaces between the rod and/or sub-rod elements of the preform. The consolidated preform may then be annealed at a temperature proximal to the glass transition temperature of the selected glass materials to remove mechanical stresses in the glass preform.

Referring back to FIG. 5, the method 200 also include a step of drawing 224 the fiber preform into the optogenetic probe. Preferably, the fiber preform is drawn into a fiber that preserves the cross sectional geometric configuration of the macroscopic preform while reducing preform feature sizes to smaller scales and producing extended fiber lengths of uniform cross section, up to 1000 meters of length or more.

Fiber drawing may be performed in a conventional fiber drawing tower at a temperature typically about 400 degrees Celsius for the $(AgPO_3)_x(WO_3)_{1-x}$ glass compound, about 400 degrees Celsius for the $TeO_2$ glass compound, about 500 degrees Celsius for the $(GeO_2)_{1-x}(PbO)_x$ glass compound, about 600 degrees Celsius for the $Ga_2O_3$ glass compound, about 500 degrees Celsius for the $Sb_2O_3$ glass compound, about 1200 degrees Celsius for the $SiO_2$ glass compound, about 600 degrees Celsius for the $NaPO_3$—$PbF_2$ glass compound, and about 600 degrees Celsius for the $NaPO_3$—$WO_3$ and $NaPO_3$—$Nb_2O_5$ glass compounds. Fiber drawing is a technique well known in the art of fiber-optics and, as will be understood by one skilled in the art, the process may be adjusted according to the glass composition of the preform and the desired final diameter of the optogenetic probe.

As mentioned above, the method 200 for fabricating an optogenetic probe according to this aspect of the invention is not limited to a particular preform configuration or preform assembly technique. Any preform configuration and preform assembly techniques that employ glass compositions $(AgPO_3)_{1-x-y}(WO_3)_xB_y$, or $(TeO_2)_{1-x}B_x$, or $(GeO_2)_{1-x-y}(PbO)_xB_y$, or $(Ga_2O_3)_{1-x}B_x$, or $(Sb_2O_3)_{1-x}B_x$, or $(SiO_2)_{1-x}B_x$, or $(NaPO_3)_{1-x-y}(PbF_2)_xB_y$, or $(NaPO_3)_{1-x-y}(WO_3)_xB_y$, or $(NaPO_3)_{1-x-y}(Nb_2O_5)_xB_y$, or a combination thereof, that are compatible for fiber co-drawing may be utilized.

As a non-limiting example of co-drawing compatibility, the electrical channels within the body of the probe may consist of glass composition $(AgPO_3)_{1-x-y}(WO_3)_xM_y$ (x=0.05, y=0.20, M=AgI) exhibiting an electrical conductance of about 0.1 milli-siemen, higher than the surrounding elongated body of glass composition $AgPO_3$—$WO_3$ and optical channels of glass composition $(AgPO_3)_{1-x}(WO_3)_x$ (x=0.02) of the probe. Such glass compositions have substantially similar softening temperatures and coefficients of thermal expansion allowing a three-material composite fiber to be drawn as a continuous viscous flow and to solidify without severe internal materials stresses.

Another non-limiting example of co-drawing compatibility may consist of electrical channels of glass composition $(AgPO_3)_{1-x-y}(WO_3)_x M_y$ (x=0.08, y=0.45, M=AgI) exhibiting an electrical conductance of about 1 milli-siemen, higher than the surrounding elongated body of glass composition $AgPO_3$—$WO_3$ and optical channels of glass composition $(AgPO_3)_{1-x-y}(WO_3)_x A_y$ (x=0.02, y=0.10, A=AgI) of the probe. Such glass compositions have substantially similar softening temperatures and coefficients of thermal expansion allowing a three-material composite fiber to be drawn as a continuous viscous flow and to solidify without severe internal materials stresses.

Still referring to FIG. 5, once the step of drawing 224 the fiber preform into the optogenetic probe is completed, shorter sections may be cut or cleaved to produce optogenetic probes of a desired length such as, for example, ranging from 1 to 20 cm in length, or any other desired length. It will be understood that additional steps of thermal drawing, chemical etching or mechanical embossing may be performed on the probes to taper down, narrow down, or otherwise tailor the profile of the shape of the distal portion 24 of the probe 10, as exemplified in FIG. 2. Embodiments of the method 200 such as that shown in FIG. 5 can enable the production of an extended-length fiber that is cut into a large number of short optogenetic probes, thus providing a cost-effective manufacturing method that can yield significant economies of scale. Macroscopic assembly of a preform is convenient and does not require exotic process techniques or equipment.

Referring back to FIG. 7, once the step of drawing 224 the fiber preform into the optogenetic probe is completed and the fiber is cut to a desired length, the method 200 may further include a step of coating 226 an inside surface of each hollow electrical channel with a metallic layer, preferably a silver layer. The step of coating 226 may performed using Tollen's reaction which, as mentioned above, is a redox chemical reaction that consists of injecting a solution composed of aqueous diamminesilver(I) complex and dextrose (preferably 2-10 mL) into the hollow channel of the probe.

More specifically, in some embodiments, the solution may be obtained by mixing silver nitrate ($AgNO_3$), potassium hydroxide (KOH), dextrose ($C_6H_{12}O_6$), ammonia ($NH_3$) and nitric acid ($HNO_3$). The solution may be injected into each hollow electrical channel using a syringe sealed to the proximal end of the probe, whereby metallic silver may be precipitated as a thin film inside the hollow channel of the probe within 5 minutes according to the following reaction:

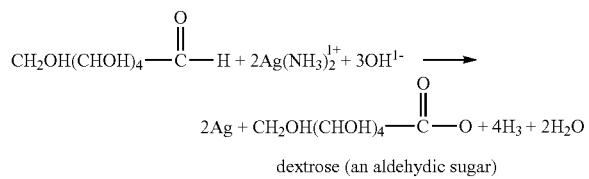

dextrose (an aldehydic sugar)

Typically, metallic silver precipitated from Tollen's reaction produce electrical channels having DC electrical sheet resistance of the order of 0.25 Ohm/Sq. As an example, the electrical conductance of a 50 μm wide, 10 cm long electrical channel may be about 1 milli-siemen using this coating technique.

Of course, numerous modifications could be made to the embodiments described above without departing from the scope of the present invention.

The invention claimed is:

1. An optogenetic probe having a proximal and a distal end, the optogenetic probe comprising:
   an elongated body made of a body glass material having a refractive index and an electrical conductivity, the elongated body extending longitudinally between the proximal and distal ends of the optogenetic probe;
   at least one optical channel extending longitudinally within the elongated body and comprising an optical channel glass material having a refractive index larger than the refractive index of the body glass material, so as to guide light therealong;
   at least one electrical channel extending longitudinally within the elongated body and comprising an electrical channel structure having an electrical conductivity larger than the electrical conductivity of the body glass material, so as to conduct electricity therealong; and
   at least one fluidic channel extending longitudinally within the elongated body and adapted for transporting fluid therealong.

2. The optogenetic probe according to claim 1, wherein the body glass material comprises a glass compound selected from the group consisting of $AgPO_3$—$WO_3$, $TeO_2$, $GeO_2$—PbO, $Ga_2O_3$, $Sb_2O_3$, $SiO_2$, $NaPO_3$—$PbF_2$, $NaPO_3$—$WO_3$, $NaPO_3$—$Nb_2O_5$, and a combination thereof.

3. The optogenetic probe according to claim 1, wherein the optical channel glass material of each optical channel comprises a glass compound selected from the group consisting of:
   $(AgPO_3)_{1-x-y}(WO_3)_x A_y$, where x≤0.30 and y≤0.70;
   $(TeO_2)_{1-x}A_x$, where x≤0.30;
   $(GeO_2)_{1-x-y}(PbO)_x A_y$, where x≤0.60 and y≤0.40;
   $(Ga_2O_3)_{1-x}A_x$, where x≤0.25;
   $(Sb_2O_3)_{1-x}A_x$, where x≤0.25;
   $(SiO_2)_{1-x}A_x$, where x≤0.40;
   $(NaPO_3)_{1-x-y}(PbF_2)_x A_y$, where x≤0.30 and y≤0.50;
   $(NaPO_3)_{1-x-y}(WO_3)_x A_y$, where x≤0.30 and y≤0.50;
   $(NaPO_3)_{1-x-y}(Nb_2O_5)_x A_y$, where x≤0.30 and y≤0.50; and
   a combination thereof,
   where A is an additive.

4. The optogenetic probe according to claim 3, wherein A comprises an additive selected from the group consisting of a transition metal oxide, an alkali metal oxide, a pnictogen metal oxide, an oxide of the elements of group 13 of the periodic table, an oxide of the elements of group 14 of the periodic table, a halogen compound, dispersed nanoparticles, and a combination thereof.

5. The optogenetic probe according to claim 4, wherein:
   the transition metal oxide is selected from the group consisting of ZnO, $WO_3$, $Nb_2O_5$, $Ti_3O_5$, $Zr_3O_5$, $Ag_2O$, $AgNO_3$, $V_2O_5$, $Cr_2O_3$, $Cu_2O$, and a combination thereof;
   the alkali metal oxide is selected from the group consisting of $Li_2O$, $Na_2O$, $K_2O$, $NaPO_3$, and a combination thereof;
   the pnictogen metal oxide is selected from the group consisting of $P_2O_5$, $Sb_2O_3$, $Bi_2O_3$, and a combination thereof;

the oxide of the elements of group 13 of the periodic table is selected from the group consisting of $In_2O_3$, $Ga_2O_3$, and a combination thereof;

the oxide of the elements of group 14 of the periodic table is selected from the group consisting of $SiO_2$, $GeO_2$, $SnO_2$, and a combination thereof;

the halogen compound is selected from the group consisting of AgI, $PbF_2$, AgCl, and a combination thereof; and the dispersed nanoparticles comprise carbon nanotubes, metallic nanoparticles, or a combination thereof.

6. The optogenetic probe according to claim 1, wherein the electrical channel structure of each electrical channel comprises one of:

an electrical channel glass material of formula $(AgPO_3)_{1-u-v}(WO_3)_u M_v$, where $u \leq 0.30$, $v \leq 0.70$, and where M is an additive, and a hollow electrical channel coated with a metallic layer.

7. The optogenetic probe according to claim 6, wherein M comprises an additive selected from the group consisting of a transition metal oxide, an alkali metal oxide, a pnictogen metal oxide, an oxide of the elements of group 13 of the periodic table, an oxide of the elements of group 14 of the periodic table, a halogen compound, dispersed nanoparticles, and a combination thereof.

8. The optogenetic probe according to claim 7, wherein:

the transition metal oxide is selected from the group consisting of ZnO, $WO_3$, $Nb_2O_5$, $Ti_3O_5$, $Zr_3O_5$, $Ag_2O$, $AgNO_3$, $V_2O_5$, $Cr_2O_3$, $Cu_2O$, and a combination thereof;

the alkali metal oxide is selected from the group consisting of $Li_2O$, $Na_2O$, $K_2O$, $NaPO_3$, and a combination thereof;

the pnictogen metal oxide is selected from the group consisting of $P_2O_5$, $Sb_2O_3$, $Bi_2O_3$, and a combination thereof;

the oxide of the elements of group 13 of the periodic table is selected from the group consisting of $In_2O_3$, $Ga_2O_3$, and a combination thereof;

the oxide of the elements of group 14 of the periodic table is selected from the group consisting of $SiO_2$, $GeO_2$, $SnO_2$, and a combination thereof;

the halogen compound is selected from the group consisting of AgI, $PbF_2$, AgCl, and a combination thereof; and the dispersed nanoparticles comprise carbon nanotubes, metallic nanoparticles, or a combination thereof.

9. The optogenetic probe according to claim 1, wherein:

the body glass material has a formula $AgPO_3$—$WO_3$;

the optical channel glass material of each optical channel comprises an optically-transparent glass material of formula $(AgPO_3)_{1-x-y}(WO_3)_x A_y$, where $x \leq 0.30$, $y \leq 0.70$, and A is an additive; and the electrical channel structure of each electrical channel comprises one of: an electrically-conductive glass material of formula $(AgPO_3)_{1-u-v}(WO_3)_u M_v$, where $u \leq 0.30$, $v \leq 0.50$, and M is an additive; and a hollow electrical channel coated with a metallic layer.

10. The optogenetic probe according to claim 1, wherein:

the body glass material has a formula $NaPO_3$—$Nb_2O_5$;

the optical channel glass material of each optical channel comprises an optically-transparent glass material of formula $(NaPO_3)_{1-x-y}(Nb_2O_5)_x A_y$, where $x \leq 0.30$, $y \leq 0.50$, and A is an additive; and the electrical channel structure of each electrical channel comprises one of: an electrically-conductive glass material of formula $(AgPO_3)_{1-u-v}(WO_3)_u M_v$, where $u \leq 0.30$, $v \leq 0.50$, and M is an additive; and a hollow electrical channel coated with a metallic layer.

11. The optogenetic probe according to claim 1, wherein:

the body glass material has a formula $TeO_2$;

the optical channel glass material of each optical channel comprises one of: an optically-transparent glass material of formula $(TeO_2)_{1-x} A_x$, where $x \leq 0.30$, and A is an additive; an optically-transparent glass material of formula $(TeO_2)_{1-x}(Na_2O)_{x-y}(ZnO)_y$, where $x=0.20$ and $y=0.10$; and an optically-transparent glass material of formula $(TeO_2)_{1-x}(Bi_2O_3)_{x-y}(ZnO)_y$, where $x=0.20$ and $y=0.15$; and the electrical channel structure of each electrical channel comprises a hollow electrical channel coated with a metallic layer.

12. The optogenetic probe according to claim 1, wherein:

the body glass material has a formula $GeO_2$—PbO;

the optical channel glass material of each optical channel comprises an optically-transparent glass material of formula $(GeO_2)_{1-x-y}(PbO)_x A_y$, where $x \leq 0.60$ and $y \leq 0.40$, and A is an additive; and the electrical channel structure of each electrical channel comprises a hollow electrical channel coated with a metallic layer.

13. The optogenetic probe according to claim 1, wherein:

the body glass material has a formula $Ga_2O_3$;

the optical channel glass material of each optical channel comprises an optically-transparent glass material of formula $(Ga_2O_3)_{1-x} A_x$, where $x \leq 0.25$, and A is an additive; and the electrical channel structure of each electrical channel comprises a hollow electrical channel coated with a metallic layer.

14. The optogenetic probe according to claim 1, wherein:

the body glass material has a formula $Sb_2O_3$;

the optical channel glass material of each optical channel comprises an optically-transparent glass material of formula $(Sb_2O_3)_{1-x} A_x$, where $x \leq 0.25$, and A is an additive; and the electrical channel structure of each electrical channel comprises a hollow electrical channel coated with a metallic layer.

15. The optogenetic probe according to claim 1, wherein:

the body glass material has a formula $SiO_2$;

the optical channel glass material of each optical channel comprises an optically-transparent material of formula $(SiO_2)_{1-x} A_x$, where $x \leq 0.25$ and A is an additive; and the electrical channel structure of each electrical channel comprises a hollow electrical channel coated with a metallic layer.

16. The optogenetic probe according to claim 1, comprising an opto-electrical channel simultaneously defining one of the at least one optical channel and one of the at least one electrical channel.

17. The optogenetic probe according to claim 16, wherein the opto-electrical channel comprises an optically-transparent and electrically-conductive glass material of formula $(AgPO_3)_{1-x-y}(WO_3)_x (AgI)_y$, where $x=0.05$ and $y=0.45$.

18. The optogenetic probe according to claim 1, further comprising a distal portion tapering toward the distal end of the probe.

19. An optogenetic system comprising:

an optogenetic probe having a proximal and a distal end, the optogenetic probe comprising:

an elongated body made of a body glass material having a refractive index and an electrical conductivity, the elongated body extending longitudinally between the proximal and distal ends of the optogenetic probe;

at least one optical channel extending longitudinally within the elongated body and comprising an optical channel glass material having a refractive index larger than the refractive index of the body glass material, so as to guide light therealong;

at least one electrical channel extending longitudinally within the elongated body and comprising an electrical channel structure having an electrical conductivity larger than the electrical conductivity of the body glass material, so as to conduct electricity therealong; and at least one fluidic channel extending longitudinally within the elongated body and adapted for transporting fluid therealong;

an optical module optically coupled to each optical channel;

an electrical module electrically coupled to each electrical channel; and a fluidic module coupled to each fluidic channel.

20. A method of fabricating an optogenetic probe, the method comprising the steps of:
a) fabricating a fiber preform comprising:
an elongated body made of a body glass material having a refractive index, an electrical conductivity, a softening temperature and a coefficient of thermal expansion;
at least one optical channel comprising an optical channel glass material having a refractive index larger than the refractive index of the body glass material, so as to transmit light therealong, and a glass softening temperature and a coefficient of thermal expansion respectively similar to the glass softening temperature and coefficient of thermal expansion of the body glass material;
at least one electrical channel comprising an electrical channel structure having an electrical conductivity larger than the electrical conductivity of the body glass material, so as to conduct electricity therealong; and
at least one fluidic channel adapted for transporting fluid therealong; and
b) drawing the fiber preform into the optogenetic probe.

21. The method according to claim 20, wherein step a) comprises:

i) providing a glass rod extending longitudinally for defining the elongated body;
ii) drilling holes longitudinally through the glass rod for defining at least one optical channel cavity, at least one electrical channel cavity and at least one fluidic channel cavity; and
iii) inserting an optical sub-rod into each optical channel cavity, thereby forming each optical channel, the optical sub-rod comprising an optical channel glass material having a refractive index larger than the refractive index of the body glass material, so as to transmit light therealong, and a glass softening temperature and a coefficient of thermal expansion respectively similar to the glass softening temperature and coefficient of thermal expansion of the body glass material.

22. The method according to claim 21, wherein step a) further comprises:
iv) inserting an electrical sub-rod into each electrical channel cavity, thereby forming each electrical channel, the electrical sub-rod comprising an electrical channel glass material having an electrical conductivity larger than the electrical conductivity of the body glass material, so as to conduct electricity therealong, and a glass softening temperature and a coefficient of thermal expansion similar to the glass softening temperature and coefficient of thermal expansion of the body glass material.

23. The method according to claim 20, wherein step a) comprises:
i) combining at least one body sub-rod, at least one optical sub-rod, at least one electrical sub-rod, and at least one fluidic sub-rod, each extending longitudinally; and
ii) drilling a hole longitudinally through each of the least one fluidic sub-rod for defining the at least one fluidic channel.

24. The method according to claim 20, wherein step a) comprises:
i) combining at least one body sub-rod, at least one optical sub-rod, at least one electrical sub-rod, and at least one fluidic sub-rod, each extending longitudinally; and
ii) drilling a hole longitudinally through each of the at least one electrical and fluidic sub-rods for defining the at least one electrical channel and the at least one fluidic channel, respectively.

* * * * *